(12) United States Patent
De Lega

(10) Patent No.: US 7,304,747 B2
(45) Date of Patent: Dec. 4, 2007

(54) METHODS AND SYSTEMS FOR DETERMINING OPTICAL PROPERTIES USING LOW-COHERENCE INTERFERENCE SIGNALS

(75) Inventor: Xavier Colonna De Lega, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 0 days.

(21) Appl. No.: 11/604,668

(22) Filed: Nov. 27, 2006

(65) Prior Publication Data

US 2007/0086019 A1 Apr. 19, 2007

Related U.S. Application Data

(62) Division of application No. 11/131,649, filed on May 17, 2005, now Pat. No. 7,142,311.

(60) Provisional application No. 60/572,010, filed on May 18, 2004.

(51) Int. Cl.
*G01B 11/02* (2006.01)
*G01B 9/02* (2006.01)

(52) U.S. Cl. .................. 356/497; 356/484; 356/511

(58) Field of Classification Search ........ 356/484, 356/496, 497, 498, 503, 511, 512, 513, 514
See application file for complete search history.

(56) References Cited

U.S. PATENT DOCUMENTS

| | | | |
|---|---|---|---|
| 5,390,023 A | 2/1995 | Biegen | |
| 5,398,113 A | 3/1995 | de Groot | |
| 6,028,670 A | 2/2000 | Deck | |
| 6,624,894 B2 | 9/2003 | Olszak et al. | |
| 6,714,307 B2 | 3/2004 | de Groot et al. | |
| 7,012,700 B2 | 3/2006 | de Groot et al. | |
| 7,046,371 B2 | 5/2006 | de Lega et al. | |
| 7,142,311 B2 * | 11/2006 | De Lega .................. | 356/497 |
| 2004/0085544 A1 | 5/2004 | de Groot | |
| 2004/0189999 A1 | 9/2004 | de Groot et al. | |

OTHER PUBLICATIONS

Peter de Groot et al., "Signal modeling for modern interference microscopes", *SPIE Proceedings* vol. 5457, pp. 26-34 (2004).
D. M. Gale et al., "Linnik microscope imaging of integrated circuit structures", *Applied Optics* vol. 35, No. 1, pp. 131-148 (Jan. 1, 1996).
Dennis C. Ghiglia et al., "Quality-Guided Path Following", *Two-Dimensional Phase Unwrapping—Theory, Algorithms and Software*, John Wiley & Sons publishers, ISBN 0-471-24935-1, pp. 122-136 (1998).
A. P. Tzannes et al., "Measurement of the modulation transfer function of infrared cameras," *Optical Engineering*, vol. 34, No. 6, pp. 1808-1817 (Jun. 1995).

* cited by examiner

*Primary Examiner*—Michael A. Lyons
(74) *Attorney, Agent, or Firm*—Fish & Richardson P.C.

(57) ABSTRACT

Methods and related systems for determining properties of optical systems (e.g., interferometers) and/or optical elements (e.g., lenses and/or lens systems) are described. For example, information related to an optical thickness mismatch of an interferometer can be determined by providing scanning interferometry data. The data typically include obtaining one or more interference signals each corresponding to a different spatial location of a test object. A phase is determined for each of multiple frequencies of each interference signal. The information related to the optical thickness mismatch is determined based on the phase for each of the multiple frequencies of the interference signal(s).

20 Claims, 16 Drawing Sheets

METHODS AND SYSTEMS FOR DETERMINING OPTICAL PROPERTIES USING LOW-COHERENCE INTERFERENCE SIGNALS

RELATED APPLICATIONS

Pursuant to 35 U.S.C. § 120, this application is a divisional of prior U.S. application Ser. No. 11/131,649, filed May 17, 2005, now U.S. Pat. No. 7,142,311, which claims the benefit of U.S. provisional application No. 60/572,010, filed May 18, 2004. The contents of the prior applications are incorporated herein by reference in their entirety.

FIELD OF THE INVENTION

The present invention is related to methods for determining properties of optical elements and/or optical systems as well as to related systems.

BACKGROUND

Scanning White Light Interferometry (SWLI), also known as vertical scanning or coherence radar, takes advantage of the fringe localization in low-coherence interferometers to profile complex surface shapes. Combining phase and coherence information for improved precision requires dedicated algorithms for dealing with possible inconsistencies between these two measurement techniques. See, for example, "Determination of Fringe Order in White-Light Interference Microscopy", Peter de Groot, Xavier Colonna de Lega, Jim Kramer, Michael Turzhitsky, Applied Optics, Volume 41, Issue 22, 4571-4578, August 2002. Some of these inconsistencies are due to geometric and chromatic aberrations that are typical of optical components. Those same aberrations are also responsible for reducing the effective lateral resolution of these profilers.

SUMMARY

Methods and systems are disclosed for an aberration characterization technique based on the frequency domain analysis of the interferograms generated by low-coherence profilers. The outputs of this analysis are field-dependent maps of the magnitude and gradient of the various lateral aberrations that affect the imaging system. This information can be used to select optimum components, detect misalignments or excentrations, and generally offer objective means of assessing the potential lateral resolution of an instrument.

In preferred embodiments, the analysis in the frequency domain of low-coherence interference signals extracts quantitative information about optical characteristics of an interferometer and its components. This information can for example be used as a feedback for an alignment procedure or to test the quality of optical subassemblies.

A first aspect is a procedure where the non-linearity of the phase of the frequency spectrum is used to calculate an optical mismatch characteristic of an interferometer. Given the optical properties (refractive index as a function of wavelength) of compensating dispersive materials present in the interferometer it is then possible to calculate a thickness correction for each material in order to obtain an interferogram having optimum contrast and phase properties. Alternatively, an iterative procedure is used to adjust the thickness of a compensating dispersive material having unknown optical properties.

Another aspect is a procedure where the non-linearity of the phase of the frequency spectrum is calculated across the entire field of view of the interferometer. The shape of the resulting non-linearity map provides information about the misalignment of optical components located inside the interferometer cavity. For example, in a Linnik interferometer, decentration of the optics results to first order in a tilt of the non-linearity map. A measure of the non-linearity gradient provides quantitative feedback for alignment.

Another aspect is a procedure where the phase and/or magnitude of two or more frequency spectrum components are used to create images of a patterned object. Image correlation techniques are then applied to measure the relative lateral displacement of image features, thus providing a measure of lateral imaging aberrations of the interferometer's imaging system. In one embodiment the technique is used to align optical components of the interferometer. In another embodiment the interferometer (for example of the Twyman-Green or Linnik type) is used to characterize optical components and assemblies.

In another aspect of the invention, a method includes providing scanning interferometry data from an interferometer. The interferometer typically includes multiple optical elements configured to reflect light from a test object that is different from the optical elements to determine information about the test object. The scanning interferometry data typically includes an interference signal including an interference intensity value for each of multiple scan positions of the interferometer. The method also includes determining a relationship between phase and frequency components of the interference signal and reducing, based on the relationship between the phase and frequency components of the interference signal, an optical thickness mismatch for a field position of the interferometer corresponding to the interference signal, the optical thickness mismatch being between the optical elements of a reference arm of the interferometer and the optical elements of a test arm of the interferometer.

Reducing the optical thickness mismatch can include adding at least one additional optical element to an optical path of the test arm or the reference arm of the interferometer. The at least one additional optical element may include a first optic formed of a first optical medium and a second optic formed of a second optical medium. Reducing the optical thickness mismatch can include determining a thickness of the additional optical element based on the relationship between the phase and frequency components of the interference signal.

Reducing the optical thickness mismatch can include changing a position of at least one the optical elements of the interferometer.

Reducing the optical thickness mismatch can include replacing one of the optical elements of the interferometer with another optical element.

Reducing the optical thickness mismatch can be performed iteratively. For example, after changing a position of at least one of the optical elements of the interferometer, one or more additional interference signals are obtained with the optical element(s) in the changed position. A relationship between phase and frequency components of the additional interference signal(s) is determined and can be compared with the relationship determined before changing the position of the optical element(s). The iterative process can also or alternatively be used with respect to adding an optical element and/or replacing at least one optical element.

Determining the relationship between phase and frequency components of the interference signal can include transforming the interference signal into a frequency domain with respect to scan values for the scan positions.

Determining the relationship between phase and frequency components of the interference signal can include determining a phase for each of multiple frequency components of the interference signal, fitting a function to the phase determined for each of the multiple frequency components, the function having at least one fitting parameter, and reducing the optical thickness mismatch based on the fitting parameter.

The scanning interferometry data can include multiple interference signals where each interference signal corresponds to a different field position of the interferometer and the method can include determining a relationship between phase and frequency components of each interference signal and reducing, based on the relationship between the phase and frequency components of the interference signal, an optical thickness mismatch for each of multiple field positions of the interferometer each corresponding to at least one of the interference signals, the optical thickness mismatch being between the optical elements of a reference arm of the interferometer and the optical elements of a test arm of the interferometer.

Reducing the optical thickness mismatch can include adding at least one additional optical element to an optical path of the test arm or the reference arm of the interferometer. The at least one additional optical element has a thickness that varies with the field position of the interferometer.

Reducing the optical thickness mismatch can include changing a position of at least one optical element of the interferometer. The at least one optical element can have a thickness that varies with the field position of the interferometer.

Each frequency component may correspond to a wavelength of light of the light source.

The interference signal can include interference intensity values obtained over a range of scan positions and the range of scan positions is greater than a coherence length of a light source of the interferometer.

Another embodiment of the invention relates to a method including providing scanning interferometry data of a test object. The scanning interferometry data includes an interference signal for each of multiple spatial locations of the test object. Each interference signal includes an interference intensity value for each of multiple scan positions of the interferometer. First information about the object is determined based on a frequency component of each of the interference signals. Second information about the object is determined based on a second frequency component of each of the interference signals. The second frequency component is typically not used in the determination of the first information about the object.

The scanning interferometry data can be obtained by a method including passing light through an optical element, and the method can further include determining information related to the optical element based on the first and second information about the test object.

The information related to the optical element may be related to a lateral aberration of the optical element.

Determining the first and second information can include transforming each interference signal into a frequency domain with respect to scan values for the scan positions of the interferometer.

The method can include determining the first information based on at least one of a phase and a magnitude corresponding to the first frequency of each transformed interference signal and determining the second information based on at least one of a phase and a magnitude corresponding to the second frequency of each transformed interference signal.

The optical element may be positioned along an optical axis of an arm of the interferometer. The optical element may be a lens system including multiple lenses.

The method can include moving the optical element relative to an optical axis of the arm of the interferometer in response to the information related to the lateral aberration.

The method can include deciding to replace the optical element with a second optical element based on the information related to the lateral aberration.

The optical element may be positioned along an optical axis between an arm of the interferometer and a detector of the interferometer.

The first frequency component of each interference signal may result from interference of light having a first wavelength and the second frequency component of each interference signal results from interference of light have a second wavelength.

The first frequency of each interference signal may result from interference of light that illuminates the test object with a first angle of incidence and the second frequency of the interference signal results from interference of light that illuminates the test object with a second, different angle of incidence.

The first information about the object may be related to a first height profile of the test object and the second information about the object is related to a second height profile of the test object. The method can include determining a first instrument transfer function of the interferometer based on the first height profile and determining a first instrument transfer function of the interferometer based on the second height profile.

The first information about the object may be related to a first reflectivity profile of the test object and the second information about the object may be related to a reflectivity height profile of the test object. The method can include determining a first modulation transfer function of the interferometer based on the first reflectivity profile and determining a first modulation transfer function of the interferometer based on the second reflectivity profile.

Another aspect of the invention relates to a method including providing first image data of an object, the first image data having been obtained by passing first light through an optical element, the first light having a first central wavelength and providing second image data of the object, the second image data having been obtained by passing second light through the optical element, the second light having a second central wavelength different from the first central wavelength. Passing second light through the optical element is typically performed after the step of passing the first light through the optical element (e.g., by varying a property of the light source and/or by modifying a filter). At least a portion of the first image data and at least a portion of the second image data are cross-correlated. Information about the optical element is determined based on the cross-correlation of the first and second image data.

The first and second image data of the object may be obtained by a method including detecting light reflected from the object, the detected light having the first central wavelength and then, detecting light reflected from the object, the detected light having the second central wavelength.

Unless otherwise defined, all technical and scientific terms used herein have the same meaning as commonly understood by one of ordinary skill in the art to which this invention belongs. All references cited herein are incorporated by reference; however, in case such references conflict with the present disclosure, the present disclosure controls.

Other features, objects, and advantages of the invention will be apparent from the following detailed description.

DETAILED DESCRIPTION

Figure 1:
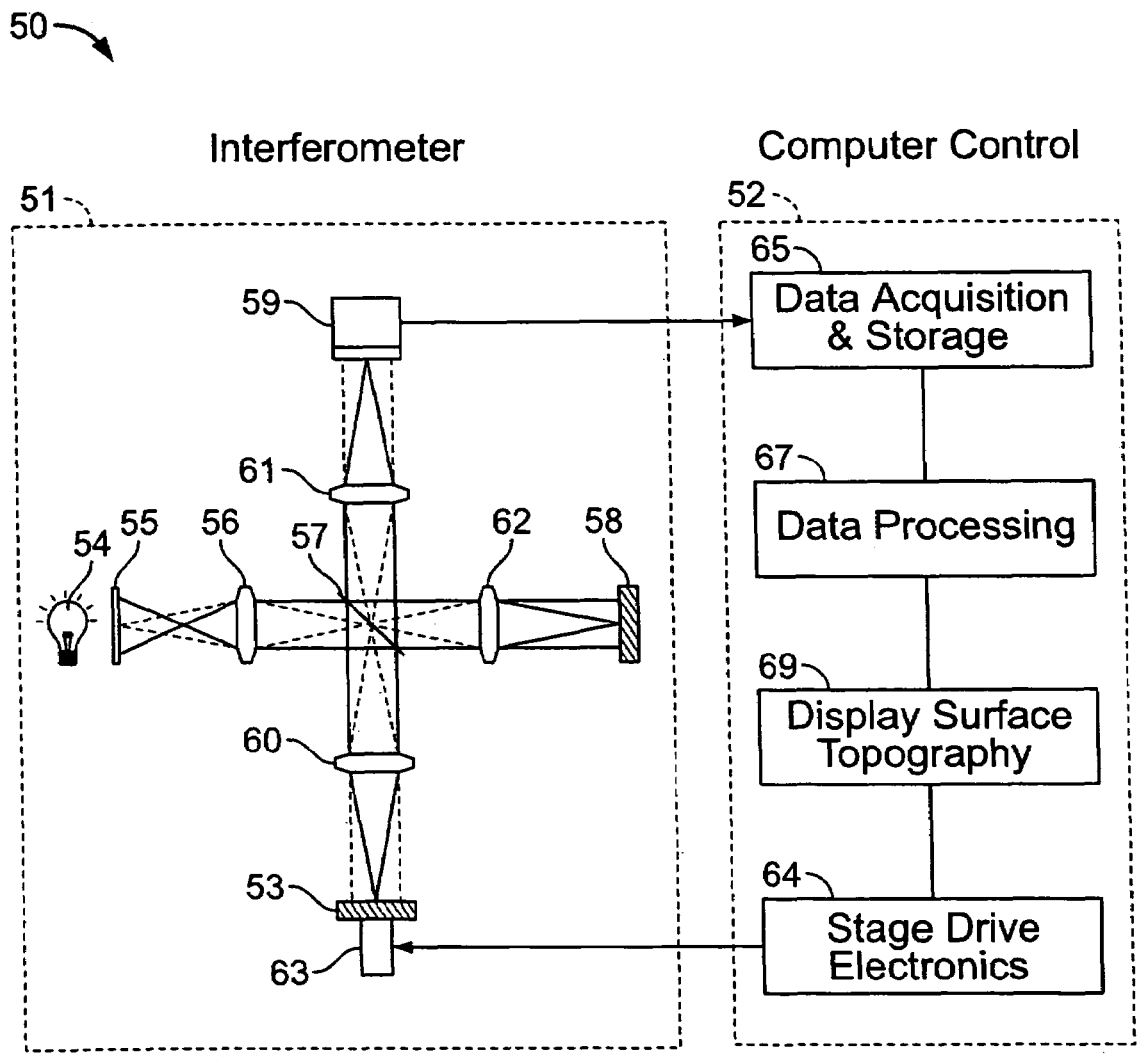
FIG. 1 illustrates an interferometer system.

Interferometers are systems that can measure the intensity of interference between light (e.g., ultraviolet light, visible light, or infrared light) reflected from one or more spatial locations of a test object (e.g., different locations about a surface of the test object) and light reflected from a reference object. The intensity of interference depends upon the optical path difference (OPD) between the light reflected from the test object and the light reflected from the reference object. Typically, an interferometer measures the intensity of interference for each of multiple different OPD values (e.g., by moving the test and/or reference objects through a number of scan position each corresponding to a different OPD value). For each spatial location of the test object, the interference intensities measured at the different OPD values define an interference signal. In low coherence interferometers, each interference signal includes multiple frequency components, each related to a different wavelength of the interfering light and/or to a different angle of incidence of the interfering light. Each interference signal can be used to determine information about the test object (e.g., the height of the spatial location corresponding to the interference signal). Information from multiple interference signals can be used to prepare information about the corresponding multiple locations of the test object (e.g., to prepare an image of the test object, a phase profile, and/or a height profile of the test object).

In practice, the interferometer can perturb the measured interference intensities. One type of perturbation results from differences (e.g., mismatches) in the thicknesses of optical media (e.g., glass and air) traversed by the light traveling along the test arm of the interferometer (e.g., the light going to and reflecting from the test object) from and the light traveling along the reference arm of the interferometer (e.g., the light going to and reflecting from the reference object). Optical thickness mismatches can result from, for example, variations in the manufacture of optical elements such as lenses (e.g., lens systems), beam splitters, and wedges that are positioned along optical paths of the interferometer and/or from the position of these optical elements (e.g., from their misalignments (e.g., excentrations). The effects tend to be large for interferometers that have many optical elements not shared by the test and reference paths. One example is a Linnik interferometer in which the test and reference paths each have a different microscope objective.

Perturbations caused by optical thickness mismatches result from the dependence of the refractive index of the mismatched optical media on the wavelength of light (e.g., from dispersion). The wavelength dependence of the refractive index can cause a frequency dependent phase shift of different frequency components of the interference signals. If neglected, the dispersion mismatch can degrade the accuracy and precision of the information determined about the test object.

Another type of perturbation includes lateral aberrations. These aberrations include wavelength dependent aberrations (e.g., lateral color) that result from the wavelength dependent focus of optical elements and the geometry dependent aberrations (e.g., spherical aberration and coma) that result from geometrical dependent focus (e.g., angle of incidence dependent focus) of optical elements. Lateral aberrations cause the light reflected from each spatial location of a test object to be focused over a wider area of a detector (e.g., as a blurry image) than in the absence of the aberrations.

As described herein, one or more interference signals can be used to determine information about one or more optical elements positioned along one or more optical paths of an interferometer.

In some embodiments, the information relates to dispersion (e.g., to a dispersion mismatch). For example, the information may be indicative of a property (e.g., refractive index and/or thickness) of one or more optical elements that can be positioned along an optical path of the interferometer to compensate for a dispersion mismatch that results from differences in the thickness of optical media traversed by light traveling along the test path and light traveling along the reference path of the interferometer. Based on the information, one or more compensating optical elements can be positioned along optical paths of the interferometer. Once the compensating optical elements having been positioned, one or more interference signals can measured. These measured interference signals can be used to determine whether, for example, different (e.g., additional or reduced) compensation is needed. For example, an iterative process may be used to determine properties of a compensating optical element that reduces the optical thickness mismatch to below a threshold value.

In some embodiments, the information determined from interference signals relates to a dispersion (e.g., a dispersion mismatch) that results from a position of one or more optics with respect to an optical axis of the interferometer. For example, the information may be indicative of a deviation of an optical element from center with respect to an optical axis and/or a deviation in longitudinal spacing between optical elements (e.g., between lenses or lens groups). The position of the optical element(s) can be changed and, optionally, interference intensities measured with the optical element in the changed position. The measured interference intensities can be used to determine, for example, whether a different position of the optical element is needed. An iterative process may be used to determine a position of the position of one or more optical elements that reduces the optical thickness mismatch to below a threshold value.

In some embodiments, the information relates to a lateral aberration (e.g., to a wavelength dependent lateral aberration and/or to a geometry dependent lateral aberration). The information can be presented as a vector map indicative of the lateral aberration over at least some (e.g., most or all) of the field of view of an optical element or optical system (e.g., of the interferometer). Such information (e.g., a vector map) can be prepared by obtaining multiple interference signals from a patterned object (e.g., an object with spatial features such as a lateral calibration standard, an object with a random rough surface, or an object with a patterned array). Each of at least two different frequency components of the interference signals are used to prepare information about the corresponding to multiple locations of the test object (e.g., to prepare an image of the test object from each frequency component, to prepare a phase profile from each frequency component, and/or to prepare a height profile of the test object from each frequency component). Typically, the information prepared using each frequency component is indicative of the locations of various surface features of the test object. However, lateral aberration generally shifts the locations as determined from the different frequency components. A correlation algorithm (e.g., a cross-correlation algorithm) can be used to compare the relative locations of surface features, and, accordingly, determine the extent of lateral aberration.

In some embodiments, the information relates to a modulation transfer function (MTF) and/or instrument transfer function (ITF) of an optical element and/or optical system (e.g., of an interferometer). The MTF and ITF are related to the point spread function of an optical system, which is also referred to as the blur spot resulting from optical and chromatic aberrations. Typically, phase and/or magnitude data determined from different frequency components of multiple interference signals are used to determine information about a patterned object. The MTF and/or ITF can be determined based on analysis of height and/or reflectivity discontinuities of the patterned object for each of multiple positions within the field of view of the optical element or optical system.

Referring now to FIG. 1, an exemplary interferometer system 50 for obtaining interference signals includes an interferometer 51 and a processor 52 (e.g., an automated computer control system). The measurement system 50 is operable to obtain an interference signal from each of multiple spatial locations of a test object 53.

Measurement system 50 includes a light source 54, a first focusing optic (e.g., one or more lenses) 56, a beam splitting element 57, a second focusing optic 62, a reference object 58, a third focusing optic 60, and a detector 59. Light source emits 54 emits spectrally-broadband light (e.g., white light), which illuminates a diffusing screen 55. First focusing optic 56 collects light from screen 55 and transmits collimated light to beam-splitting element 57, which splits the collimated light into first and second portions. A first portion of the collimated light is received by second focusing optic 62, which focuses the first portion of the light onto reference object 58. Light reflected from the reference object is received by second focusing optic 62, which transmits collimated light reflected by the reference object 58 back to beam-splitting element 57. Beam-splitting element 57 directs the second portion of the collimated light to third focusing optic 60, which focuses the light onto test object 53. Light reflected from test object 53 is received by third focusing optic 60, which transmits collimated light reflected by test object 53 back to beam-splitting element 57. Beam-splitting element 57 combines light reflected from reference object 58 and test object 53 and directs the combined light to a fourth focusing optic 61, which focuses the combined light to a detector 59.

Detector 59 is typically a multidimensional detector (e.g., a charge coupled device (CCD) or charge injection device (CID)) having a plurality of detector elements (e.g., pixels) arranged in one or more dimensions (e.g., two dimensions). Optics 60 and 61 focus light reflected from test object 53 onto detector 59 so that each detector element of detector 59 receives light reflected from a corresponding spatial location (e.g., a point or other small region) of test object 53. Light reflected from respective spatial locations of test object 53 and light reflected from reference object 58 interferes at detector 59. Each detector element produces a detector signal related to the intensity of the interfering light.

System 50 is configured to measure interference signals related to spatial locations of test object 53. Typically, system 50 creates an OPD between light reflected from reference object 58 and light reflected from test object 53. For example, test object 53 can be displaced through a number of scan positions along a scan dimension axis by a scan mechanism (e.g., an electromechanical transducer 63 (e.g., a piezoelectric transducer (PZT)), and associated drive electronics 64) controlled by computer 52. In some embodiments, a scan position increment between successive scan positions is at least about $\lambda/15$ (e.g., at least about $\lambda/12$, at least about $\lambda/10$), where $\lambda$ is a mean wavelength of the light detected at each pixel.

For each scan position, detector 59 outputs an intensity value (e.g., the intensity detected by a given detector element) for each of multiple different spatial locations of the test object. Taken along the scan dimension, the intensity values for each spatial location define an interference signal corresponding to the spatial location. The intensity values corresponding to a common scan position define a data set (e.g., an interferogram) for that scan position. The spectral distribution of the light source (e.g., the range of emission wavelengths), the geometric properties of optical elements of the interferometer (e.g., the angles of incidence with which the light is received and transmitted by the optical elements), the optical properties of optical elements of the interferometer (e.g., the wavelength dependence of the refractive index of refractive optical elements), and the spectral response of the detector define an effective frequency spectrum for interference signals obtained using the interferometer. This effective spectrum is nominally centered at a wavenumber $k_0$.

Figure 2:
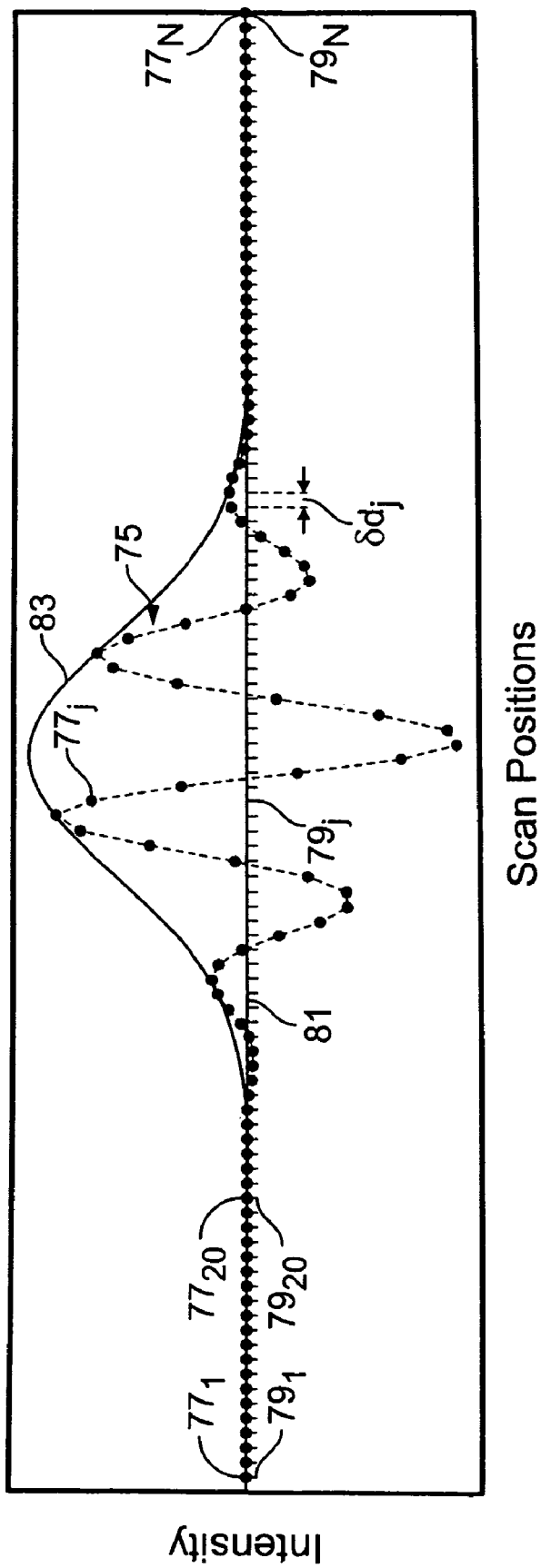
FIG. 2 illustrates an interference signal obtained with an interferometer and corresponding to a single spatial location of a test object.

Referring to FIG. 2, an exemplary interference signal 75 includes an interference intensity value 77$j$ for each of N scan positions 79$_i$ along a scan dimension axis 81. The intensity values 77$j$ of interference signal 75 correspond to a single spatial location of a test object. Intensity values 77$j$ map out a number of oscillations (e.g., fringes), which decay on either side of a maximum according to a low coherence envelope 83, which does not expressly appear in such interference signals but is shown for clarity of discussion. The width of coherence envelope 83 corresponds generally to the coherence length of the detected light, which is related to the effective spatial frequency spectrum of the interferometer. Among the factors that determine the coherence length are temporal coherence phenomena related to, for example, the spectral bandwidth of the light, and spatial coherence phenomena related to, for example, the range of angles of incidence of light illuminating the test object. Techniques for determining information about a test object based on interference signals include transform-based methods (e.g., frequency domain analysis (FDA) as described in U.S. Pat. No. 5,398,113 to de Groot, the contents of which patent is incorporated herein by reference).

As can be seen from FIG. 2, interference signal 75 results from detecting intensity values over a range of scan positions 79$j$ that is greater than about ¾ of the width of the coherence envelope. In some embodiments, the intensity values are detected over a range of scan positions that is greater than the width of the coherence envelope and, therefore, greater than the coherence length of the detected light.

Because the spectral bandwidth of the interfering light includes multiple wavelengths λ, interference signal 75 includes contributions from interference at multiple frequencies k. Each interference frequency can be expressed as a wavenumber k=2π/λ, where λ is the wavelength of the light that results in interference at the wavenumber k. As discussed above, a possible interference signal distortion results from a combination of optical thickness mismatches and the wavelength dependence of the refractive index of optical media traversed by light reflected from the test object and light reflected from the reference object. For each frequency k, a phase shift φ(k) can be expressed as:

$$\varphi(k) = 2k \sum_i n_i(k) \Delta t_i \quad (1)$$

where $n_i(k)$ is the refractive index of the $i^{th}$ medium traversed by light traveling along the test and reference paths at the wavelength corresponding to wavenumber k, and $\Delta t_i$ is the thickness difference of the $i^{th}$ medium between the test and reference path.

In an ideal interferometer, the $\Delta t_i$ factors corresponding to optical media (e.g., glass (e.g., BK7, SFL6, fused silica)) are all equal to zero so that no phase shift results from thickness mismatches. In practice, the thicknesses of optical media along the test and reference arms are typically at least partially mismatched so that the $\Delta t_i$ factors are non-zero (e.g., the light traveling along one of the test and reference arms travels a greater distance through at least one optical medium than the light traveling along the other arm). As discussed next, however, an interference signal can be used to determine properties (e.g., refractive index and thickness) of a compensating optical element that, when positioned along an optical path of the interferometer, reduces the $n_i(k) \Delta t_i$ factors (e.g., causes the $n_i(k) \Delta t_i$ factors to sum to about zero) and can reduce (e.g., eliminate) optical thickness mismatches of an interferometer.

Expressing Eq. as a Taylor expansion about the central source frequency $k_0$ yields:

$$\varphi(k) \approx 2k_0 \sum_i n_i(k_0) \Delta t_i + \quad (2)$$
$$2(k - k_0) \sum_i \left( n_i(k_0) \Delta t_i + k_0 \frac{\partial n_i}{\partial k}(k_0) \Delta t_i \right) +$$
$$(k - k_0)^2 \sum_i \left( 2 \frac{\partial n_i}{\partial k}(k_0) \Delta t_i + k_0 \frac{\partial^2 n_i}{\partial k^2}(k_0) \Delta t_i \right) + \ldots$$

where the term $\partial n_i/\partial k$ is the 1$^{st}$ derivative of the refractive index of the ith optical medium with respect to the wavelength corresponding to the interference frequency k and the term $\partial^2 n_i/\partial k^2$ is the 2$^{nd}$ derivative of the refractive index of the ith optical medium with respect to the wavelength corresponding to the interference frequency k. The first term in the Taylor expansion is a constant phase factor. The second term is a linear function of wavenumber k, which is related to the group velocity index and corresponds to a shift of the position at which maximum fringe contrast of the interference signal is observed as a function of interferometer scan position. The second term does not affect interference contrast or the shape of the modulation envelope. The third term in the Taylor expansion, however, represents nonlinearity (e.g., parabolic nonlinearity) of the relationship between phase and frequency components of the interference signal. Such nonlinearity is indicative of a dispersion mismatch of the test and reference arms of the interferometer. The phase shifts, which are typically different for each frequency k, reduce the contrast of the interference signal and spread the interference signal over a larger range of OPD than would otherwise be observed. As discussed next, the third and/or higher terms of Eq. 3 can be used to determine information about the optical thickness mismatches and to determine, for example, properties (e.g., 1st and 2nd order derivatives of refractive index with respect to wavelength, thickness. and/or shape) of compensating optical elements that reduce (e.g., eliminate) the phase shifts caused by the mismatches.

Typically, the method for determining information about optical thickness mismatches includes obtaining one or more interference signals using an interferometer. Each interference signal corresponds to a different spatial location of a test object. For each interference signal, the phase of each of multiple frequencies of the interference signal is determined. For example, the phase of different frequencies of an interference signal can be determined by Fourier transformation of the interference signal. The phases of different frequencies of the interference signal are fit (e.g., by least squares) to function that includes one or more fitting parameters that are related to the optical thickness mismatches between the test and reference arms of the interferometer. The fitted parameters are used to determine a property (e.g., 1st and 2nd order derivatives of refractive index with respect to wavelength, thickness, and/or shape) of one or more optical elements (e.g., plates, wedges, lenses, beam splitters) that can be positioned along an optical path of the interferometer to compensate for (e.g., reduce or eliminate) the dispersion mismatch.

We now discuss an exemplary method for determining information about optical thickness mismatch beginning by presenting an interference signal obtained with an interferometer exhibiting such mismatches.

Figure 3:
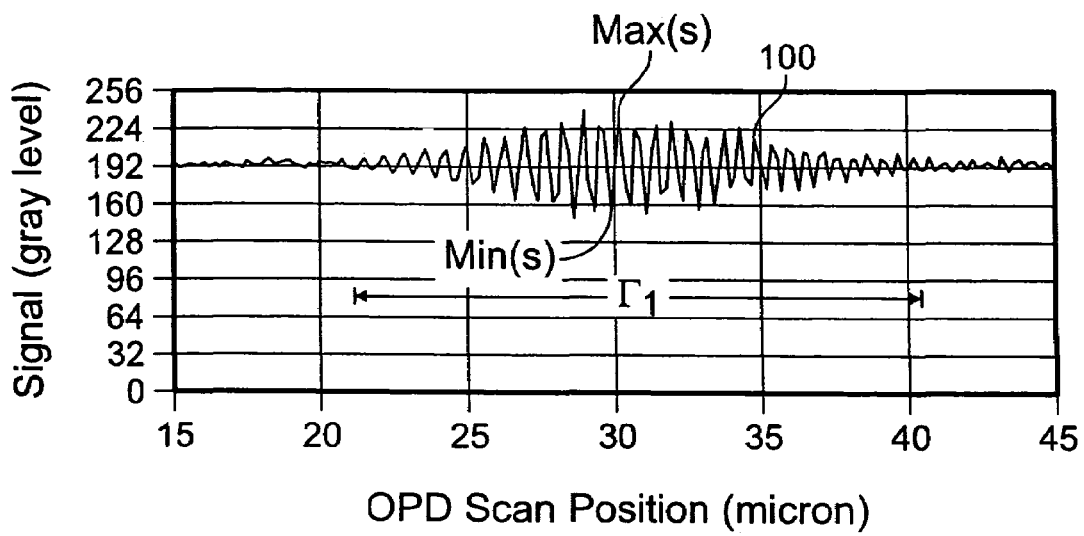
FIG. 3 illustrates an interference signal obtained with an interferometer and corresponding to a single spatial location of a test object.

Referring to FIG. 3, an interference signal 100 is an example of an interference signal that corresponds to a single spatial location of an object as obtained using an interferometer having an endoscopic objective positioned along each arm. The interferometer uses a broadband light source. Such interferometers are typically used to measure spheres and cones, and are similar to Linnik interferometers in that many optical elements are positioned along both the test and reference arms of the interferometer. Interference signal 100 includes intensity values measured over a range of scan positions corresponding to an OPD of about 30 microns, but exhibits substantial interference intensity over a smaller range r1 corresponding to an OPD of about 20 microns.

Interference signal 100 has a fringe contrast C given by:

$$C = \frac{\max(s) - \min(s)}{\max(s) + \min(s)} \qquad (3)$$

where s is an intensity of the measured interference signal. The contrast C, as defined by equation (3) is equal to 23.8%.

Continuing with the method, interference signal 100 is transformed (e.g., by Fourier transformation) into an inverse dimension with respect to the values for the OPD's along the scan dimension. The phase is determined for each of multiple frequencies of the transformed interference signal. Typically, most (e.g., all) of the multiple frequencies for which the phase is determined correspond to frequencies that correspond to different wavelengths of the spectrum of the light source of the interferometer.

Figure 4:
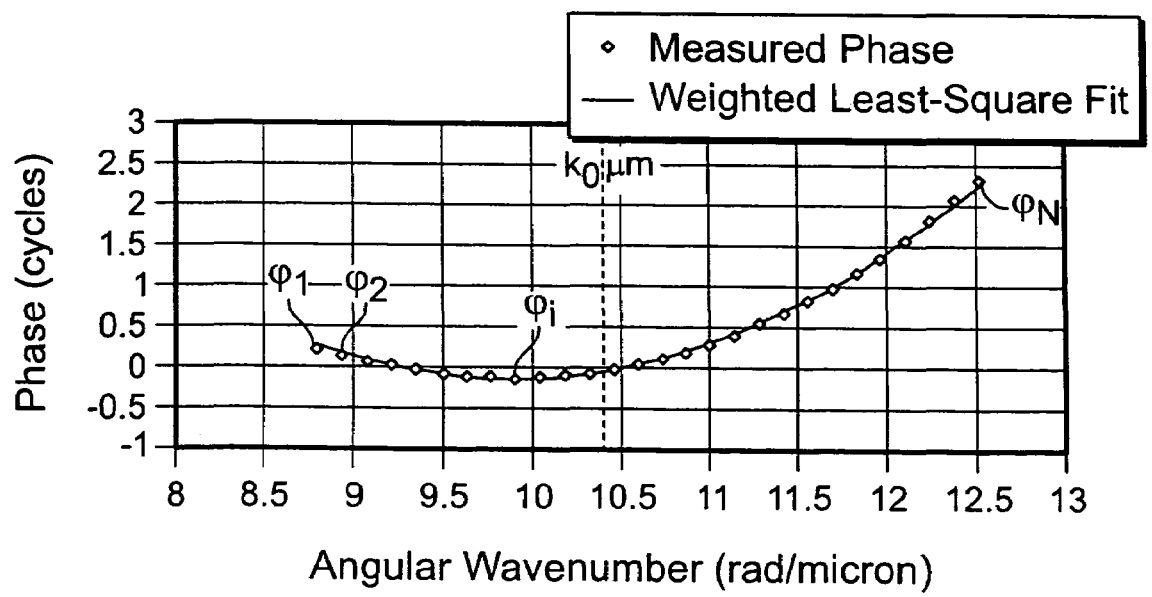
FIG. 4 illustrates phase vs. frequency data for the interference signal of FIG. 3.

FIG. 4 shows a plot of phase $\phi(k)$ vs. frequency data (in units of cycles equal to $2\pi$ radians) for each of N different frequencies k of the interference signal. The plot shows a clear nonlinear (e.g., parabolic) shape due to an optical medium thickness imbalance in the two arms of the interferometer used to obtain interference signal 100. The phases $\phi(k)$ in FIG. 4 are fit to a second order polynomial function according to:

$$\phi(k) = A_0 + A_1(k-k_0) + A_2(k-k_0)^2 \qquad 4$$

where $k_0$ is the central wavelength of the effective spatial frequency spectrum of the interferometer and $A_0$, $A_1$, and $A_2$ are the fitting parameters. Such a fit can be performed by, for example, a weighted least squares fitting routine with each phase $\phi(k)$ weighted by the square of the Fourier amplitude of the corresponding frequency k. The solid line in FIG. 4 is determined from the fitting parameters determined from a weighted least squares fit of Eq. 4 to the phases $\phi(k)$.

The fitting parameters $A_0$, $A_1$, and $A_2$ correspond to the first, second, and third order components of the Taylor expansion seen in Eq. 2. In particular, the third order fitting parameter $A_2$ can be expressed as:

$$A_2 \approx \sum_i \left( 2\frac{\partial n_i}{\partial k}(k_0)\Delta t_i + k_0 \frac{\partial^2 n_i}{\partial k^2}(k_0)\Delta t_i \right) \qquad 5$$

Eq. 5 can be rearranged to determine a thickness $\Delta t_c$ of a single optical medium (e.g., an optical glass (e.g., BK7) or fused silica (e.g., SF6)) that compensates for the optical thickness mismatch between the test and reference arms of the interferometer:

$$\Delta t_c = \frac{-A_2}{2\frac{\partial n_c}{\partial k}(k_0) + k_0 \frac{\partial^2 n_c}{\partial k^2}(k_0)} \qquad 6$$

where $\partial n_c/\partial k$ is the $1^{st}$ derivative of the refractive index of the compensating medium with respect to the wavelength corresponding to frequency k and the term $\partial^2 n_c/\partial k^2$ is the $2^{nd}$ derivative of the refractive index of the compensating medium with respect to the wavelength corresponding to frequency k. For a given optical medium, the $\partial n_c/\partial k$ and $\partial^2 n_c/\partial k^2$ can be determined from its Sellmeier coefficients, which describe the relationship between refractive index and wavelength for an optical medium.

To use Eq. 6, a compensating optical medium (e.g., an optical glass (e.g., BK7) or fused silica (e.g., SFL6)) is typically selected. The $\partial n_c/\partial k$ and $\partial^2 n_c/\partial k^2$ of the optical medium are determined (e.g., from the Sellmeier coefficients of the medium) and substituted into Eq. 6, which is then solved for the thickness $\Delta t_c$. Based on the fit of Eq. 4 to the phases $\phi(k)$ of FIG. 4, Eq. 6 predicts that a BK7 optical element (e.g., optical plate) having a thickness $\Delta t_c$ of about 190 microns will compensate for the optical thickness mismatch of the interferometer used to obtain interference signal 100 if the optical element is positioned along one of the arms of the interferometer. To compensate for the optical thickness mismatch, the compensating optical element is typically positioned along the interferometer arm in which the total optical medium thickness is too small.

The interferometer arm along which the compensating optical element should be positioned to compensate for the thickness mismatch can be identified by taking into account the arm along which the OPD is varied (e.g., scanned) to obtain the interference signal, the sign of the OPD variation, and the sign convention used for determining the inverse transform of the interference signal. Alternatively, a plot of $\phi(k)$ vs. frequency can be determined from an interference signal obtained with the compensating optic positioned along one of the interferometer arms. The non-linearity of the $\phi(k)$ data shows readily if the correct arm is compensated.

The extent of nonlinearity of phase $\phi(k)$ vs. frequency data can be expressed as an objective parameter $\epsilon\phi$. For example, $\epsilon\phi$ can determined based on the difference between the phases $\phi(k)$ and a fit to the phases (e.g., the difference between the phases $\phi(k)$ and the least squares fit of Eq. 4 to the phases). In some embodiments, $\epsilon\phi$ is given by the peak-to-valley range of the difference between phases $\phi(k)$ and a fit to the phases. In some embodiments, $\epsilon\phi$ is related to the squared differences between the phases $\phi(k)$ and a fit to the phases. For example, $\epsilon\phi$ can be expressed as the $\chi^2$ sum of residuals or the standard deviation between the phases $\phi(k)$ and a fit to the phases. Typically, the optical thickness mismatch compensation method aims at reducing $\epsilon\phi$ below a given threshold.

Figure 5:
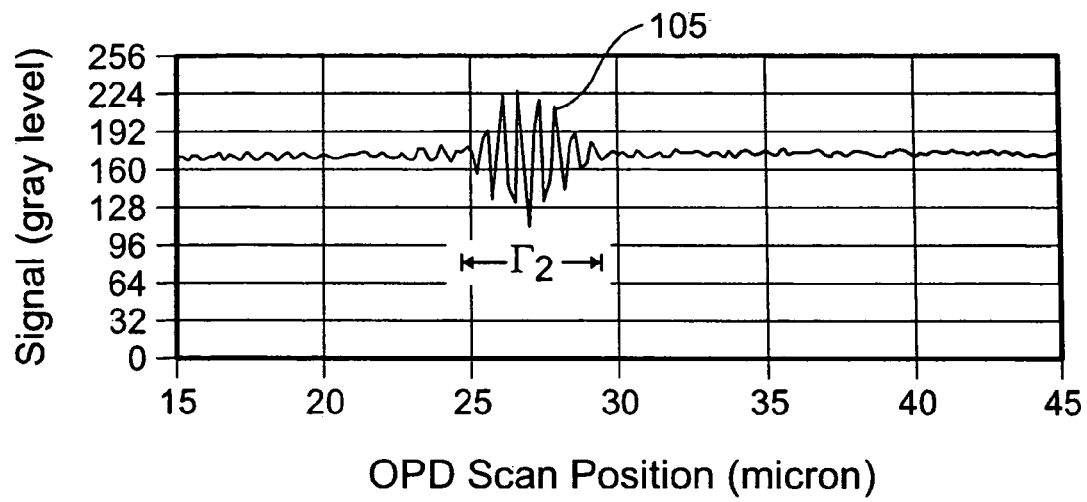
FIG. 5 illustrates an interference signal obtained with the interferometer used to obtain the interference signal of FIG. 3 but after positioning a compensating optical element along an arm of the interferometer.

FIG. 5 shows an interference signal 105 obtained with the same interferometer used to obtain interference signal 100 of FIG. 3 but with a 210-micron thick BK7 plate positioned along the interferometer arm in which the total optical medium thickness was too small. Interference signal 105 has a higher contrast C of 33.3% than interference signal 100 (FIG. 3) and exhibits substantial interference intensity over a range r2 of OPD variation that is narrower than the range r1 of interference signal 100. In low coherence interferometry, a narrower higher contrast interference signal (e.g., interference signal 105) typically provides better precision and accuracy than a wider lower contrast interference signal (e.g., interference signal 100).

Figure 6:
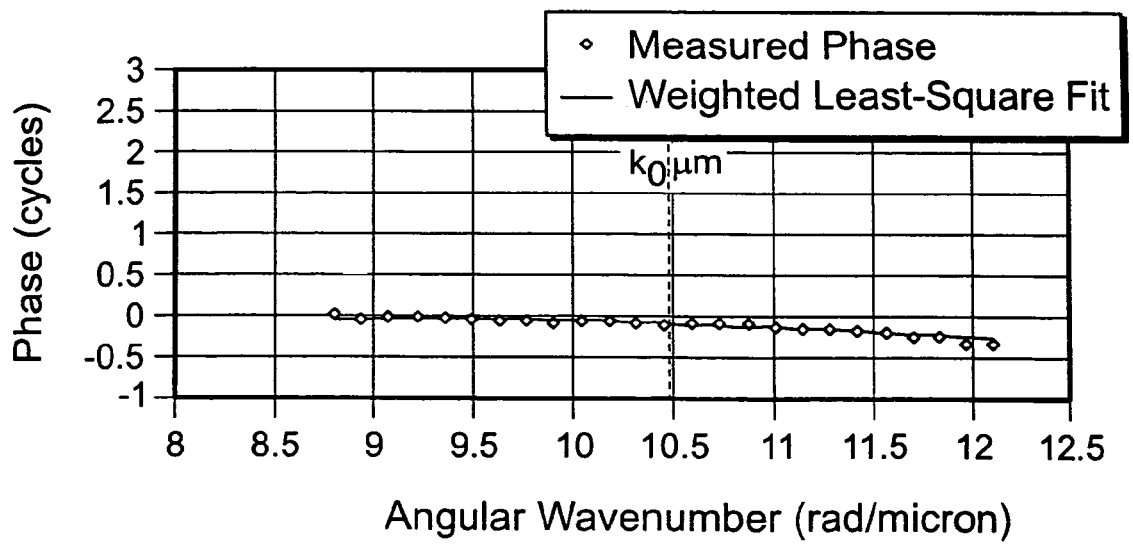
FIG. 6 illustrates phase vs. frequency data for the interference signal of FIG. 3.

FIG. 6 shows a phase $\phi(k)$ vs. frequency plot as determined from the Fourier transform of interference signal 105 (FIG. 5). The phase $\phi(k)$ vs. frequency data of FIG. 6 exhibits substantially less non-linearity (e.g., less curvature) than the phase $\phi(k)$ vs. frequency data (FIG. 4) determined from interference signal 100 (FIG. 3).

Because interference signal 105 was obtained with a compensating optic having a thickness of 210 microns rather than the optimal 190 microns predicted by Eq. 6, the phases $\phi(k)$ of FIG. 6 exhibit some residual nonlinearity (e.g., negative curvature) with respect to frequency. Based on a least squares fit of Eq. 4 to the phases $\phi(k)$ determined from interference signal 105 (this fit is shown as the solid line of FIG. 6), Eq. 6 predicts that a BK7 optical element (e.g., optical plate) having a thickness $\Delta tc=20$ microns (e.g., 210 microns-190 microns) can be positioned along the other arm of the interferometer to compensate for the optical thickness mismatch introduced by the too thick compensating optical element. Of course, one could alternatively replace the 210 microns thick compensating optical plate with a plate 190 microns thick.

As discussed above, the effective spectrum of an interferometer can depend on both temporal coherence effects related to the source spectral width and spatial coherence effects related to the source dimensions and angles of incidence. Information related to the optical thickness mismatch of such interferometers is typically determined by reducing spatial coherence effects (e.g., by using a sufficiently small source emitting area). Once the optical thickness mismatch has been determined and compensated, the source dimension is restored to whatever size is required for normal operation of the interferometer.

While Eq. 6 has been described as predicting a property (e.g., a thickness $\Delta tc$) of a single compensating optical element, more than one optical element can be used to compensate for optical thickness mismatch. For example, a different optical element (e.g., plate) can be placed along each arm of the interferometer, where the difference in thicknesses of the optical elements corresponds to $\Delta tc$. As an example, if $\Delta tc$ is predicted to be 75 microns, an optical element having a thickness of 500 microns can be positioned along one arm of the interferometer and an optical element having a thickness of 575 microns can be positioned along the other arm of the interferometer.

While Eq. 6 has been described as being applied to a compensating optical medium with known optical properties (e.g., known $1^{st}$ and $2^{nd}$ order derivatives of refractive index with respect to wavelength), other methods can be used. For example, Eq. 6 can be used even if the optical properties of the optical medium are not known. Typically, phase $\phi(k)$ vs. frequency data (e.g., as shown in FIG. 4) are determined from one or more interference signals obtained using an interferometer. Phase $\phi(k)$ vs. frequency data are also determined from one or more interference signals obtained using the interferometer with a compensating optical element positioned along one of the optical arms of the interferometer. Here, the compensating optical element typically has a known thickness and shape, but may have other unknown optical properties (e.g., unknown $1^{st}$ and $2^{nd}$ order derivatives of refractive index with respect to wavelength). Eq. 4 is fit to the $\phi(k)$ vs. frequency data determined with and without the compensating optical element. The unknown optical properties (e.g., the $1^{st}$ and $2^{nd}$ order derivatives of refractive index with respect to wavelength) of the optical medium are determined from the fitted parameters (e.g., from the fitted parameters $A_2$). Alternatively, a similar method can be used to determine a thickness and/or shape of an optical element having known refractive index properties.

While the method for compensating for optical thickness mismatch has been described as using the second order term of the Taylor expansion of Eq. 2, other orders can be used. For example, phase $\phi(k)$ vs. frequency data (e.g., FIG. 4) can be fit to a function (e.g., a polynomial of higher than $2^{nd}$ order) having more or different parameters than Eq. 4. The fitted parameters are related to higher order terms of the Taylor expansion of Eq. 2 (e.g., $3^{rd}$, $4^{th}$, $5^{th}$, and/or higher order terms) just as Eq. 6 relates the fitted parameter $A_2$ of Eq. 4 to the $2^{nd}$ order term of the Taylor expansion in Eq. 3. The relationship between the fitted parameters and the higher order terms of the Taylor expansion are used to determine optical properties of compensating media.

While a method for determining a property (e.g., a thickness and/or derivatives of refractive index with respect to wavelength) of a compensating optical element has been described as including a fit to phase $\phi(k)$ vs. frequency data, other methods can be used. For example, in some embodiments, properties of a compensating optical element that reduces (e.g., eliminates) optical thickness mismatch are determined without fitting phase vs. frequency data. The method can be performed iteratively. Typically, the method includes providing one or more first interference signals obtained using an interferometer. Phase $\phi(k)$ vs. frequency data are determined from the one or more first interference signals. A compensating optic is introduced along one or both of the arms of the interferometer. One or more second interference signals are obtained with the compensating optic in position. Phase $\phi(k)$ vs. frequency data are determined from the one or more second interference signals. The next step of the method typically includes comparing the phase $\phi(k)$ vs. frequency data obtained from the first and second interference signals to determine whether the compensating optic increased or decreased the optical thickness mismatch. Such a determination can be made, for example, based on the extent of nonlinearity of the phase $\phi(k)$ vs. frequency data. Typically, decreased nonlinearity of the phase $\phi(k)$ vs. frequency data indicates decreased optical thickness mismatch. The process of obtaining interference signals with different compensating optical elements (e.g., optical elements of different thickness or material) can continue iteratively until phase $\phi(k)$ vs. frequency data having a desired degree of linearity are obtained. Hence, the nonlinearity of the phase $\phi(k)$ vs. frequency data can act as a feedback mechanism for conducting an iterative compensation of optical thickness mismatch.

While optical thickness mismatch compensation has been described as using one or more compensating optical elements each formed of the same optical medium, more than one optical medium can be used to compensate for optical thickness. Use of more than one optical medium can be beneficial with, for example, interferometers having many different optical elements located on the test and reference arms. A compensating optical element of a single optical medium may not sufficiently reduce (e.g., eliminate) the optical thickness mismatch of such interferometers.

Typically, the method for using more than one. optical medium to compensate for optical thickness mismatch includes using an interferometer to obtain one or more interference signals and determining phase $\phi(k)$ vs. frequency data from the one or more interference signals. The phase $\phi(k)$ vs. frequency data are fit to a function having parameters that correspond to compensating optical elements of different optical media (e.g., different types of optical glass or fused silica). Properties (e.g., refractive index, thickness, and/or shape) of the compensating optical elements are determined from the fitted parameters. Compensating optical elements of two or more different media are positioned along one or more optical paths of the interferometer. The interferometer is used to obtain one or more interference signals with the compensating optical elements in position and phase $\phi(k)$ vs. frequency data are determined from the interference signal(s). The remaining optical thickness mismatch can be evaluated by, for example, the parameter $\epsilon\phi$ to determine whether different compensation is needed.

We now discuss an example for compensating optical thickness mismatch using different optical media by comparing results obtained from compensation with a single optical medium and results obtained by compensation with two optical media.

Figure 7:
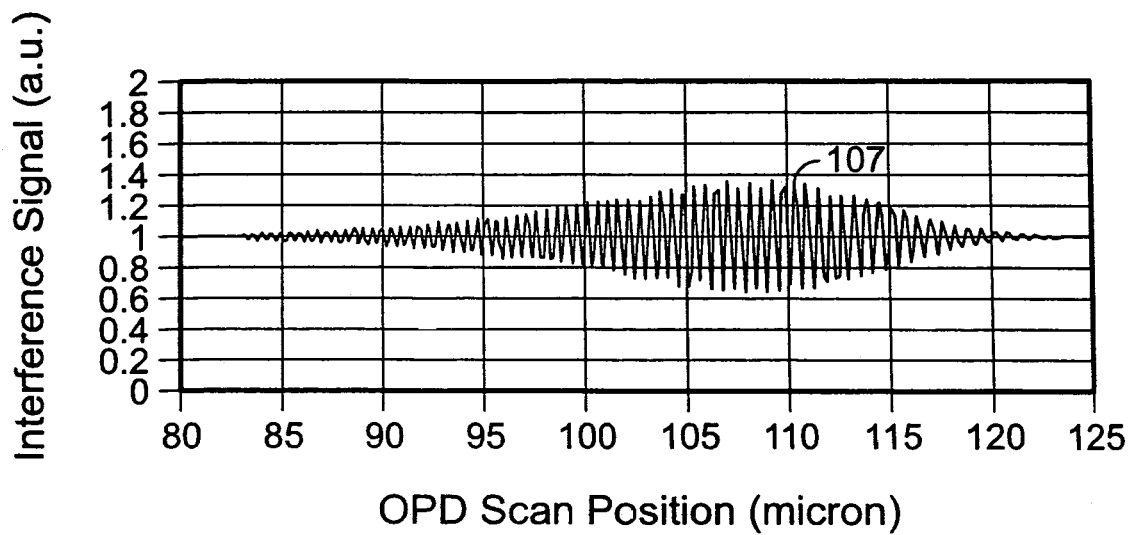
FIG. 7 illustrates an interference signal obtained with an interferometer and corresponding to a single spatial location of a test object.

Referring to FIG. 7, an interference signal 107 is simulated as if obtained from a Linnik interferometer having a 100× microscope objective (0.94 NA) positioned along its test arm and along its reference arm. Each simulated objective included eleven optical elements (e.g., lenses). Small thickness variations were introduced into the eleven elements.

Figure 8:
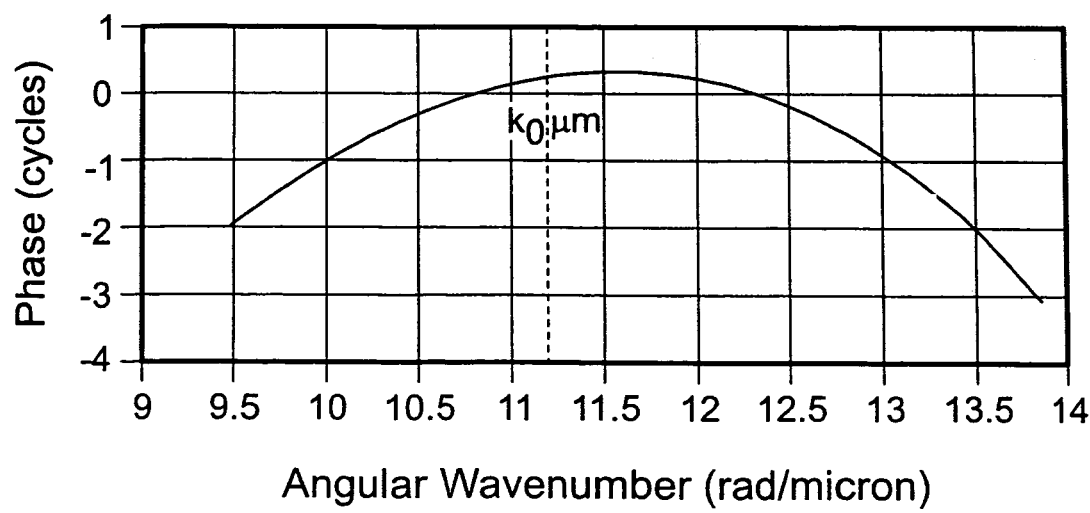
FIG. 8 illustrates phase vs. frequency data for the interference signal of FIG. 7.

FIG. 8 illustrates phase $\phi(k)$ vs. frequency data determined from interference signal 107 by Fourier transformation into an inverse dimension with respect to OPD. Eq. 4 was fit to the phase $\phi(k)$ vs. frequency data of FIG. 8 and the thickness $\Delta tc$ of a compensating optical element formed of a single optical medium (SFL6) determined using Eq. 6.

Figure 9:
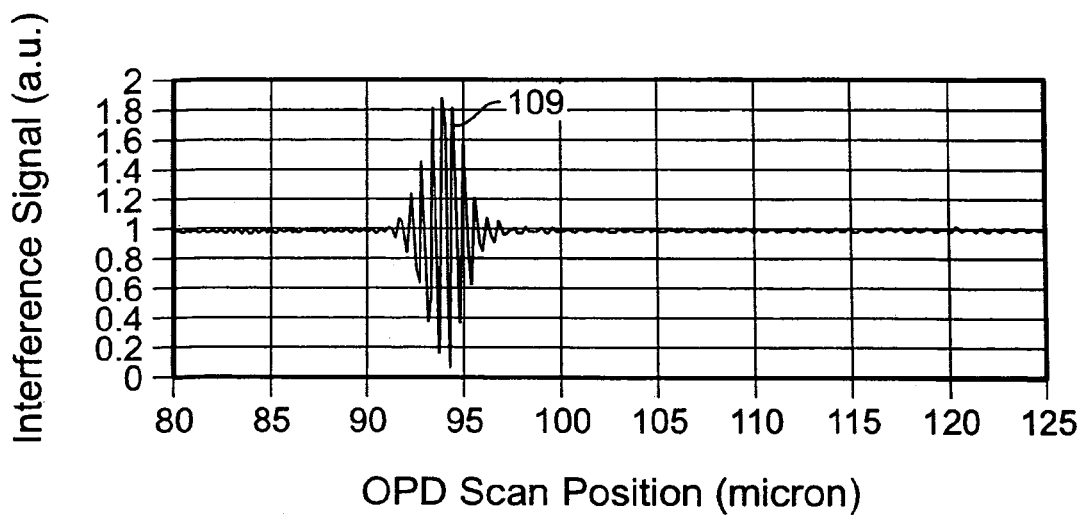
FIG. 9 illustrates an interference signal obtained with the interferometer used to obtain the interference signal of FIG. 7 but after positioning a compensating optical element formed of a single optical medium along an arm of the interferometer.

Referring to FIG. 9, an interference signal 109 is simulated as if obtained from the Linnik interferometer used to obtain interference signal 107 of FIG. 7 but with the single compensating optical element in position. The contrast C of interference signal 109 is 94.3% compared to the contrast C of interference signal 107 of 35.6%.

Figure 10:
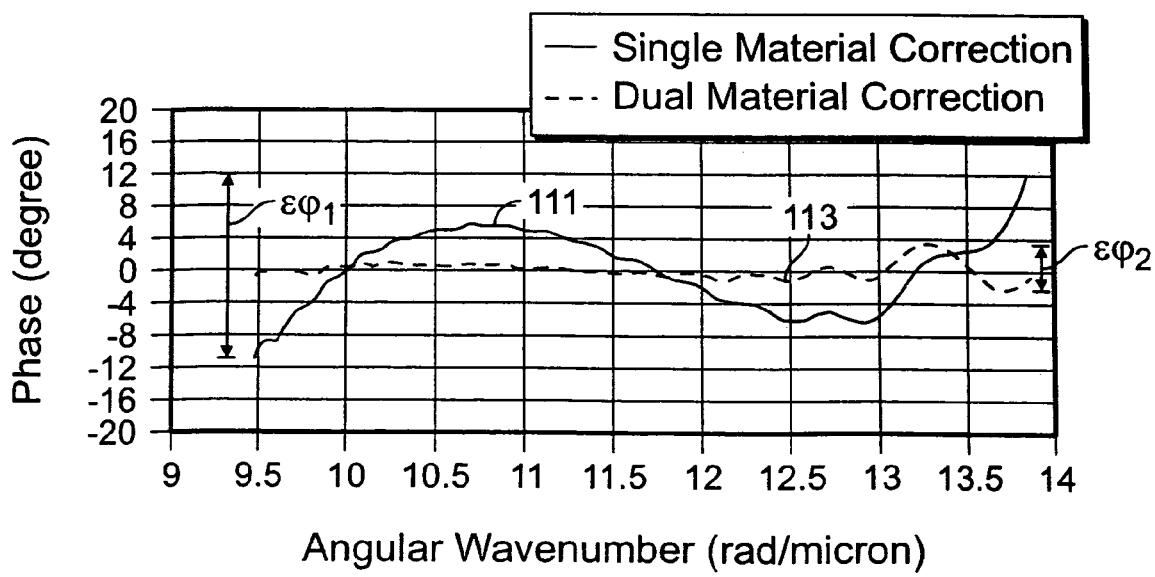
FIG. 10 illustrates residuals related to the phase vs. frequency data of FIG. 8.

Referring to FIG. 10, a line 111 indicates the difference in units of degrees between the phase $\phi(k)$ vs. frequency data of FIG. 8 and a fit determined from parameters $A_0$, $A_1$, and $A_2$, of Eq. 4. The extent of nonlinearity $\epsilon\phi_1$ of line 111 as determined by the peak-to-valley range of the difference between phases $\phi(k)$ and the fit to the phases is about 20°.

The thicknesses of compensating optical elements of two different optical media can be determined by fitting phase $\phi(k)$ vs. frequency data to function that includes the refractive index as a function of frequency k for each optical medium:

$$\phi(k)=B_0+B_1k+M_1(k)\Delta t_1+M_2(k)\Delta t_2 \qquad 7$$

where $B_0$ and $B_1$ are constants, $\Delta t_1$ is the thickness of the compensating optical element formed of the first optical medium, $\Delta t_2$ is the thickness of the compensating optical element formed of the second optical medium, and $M_1(k)$ and $M_2(k)$ are related to the index of refraction of each optical medium by:

$$M_i(k)=2k(n_i(k)-n_{ambient}(k))i=1,2 \qquad 8$$

where $n_{ambient}$ is the index of refraction of the medium where the correction takes place (e.g., air) and $n_i$ is the refractive index of the compensating optical medium at the wavelength of light corresponding to frequency k.

Eq. 7 can be fit to the phase $\phi(k)$ vs. frequency data by, for example, a least squares fitting routine that minimizes the sum:

$$\chi^2 = \sum_k (B_0 + B_1k + M_1(k)\Delta t_1 + M_2(k)\Delta t_2 - \varphi(k))^2 \qquad 9$$

Eq. 7 is fit to the phase $\phi(k)$ vs. frequency data of FIG. 8 using BK7 in addition to SFL6. As seen in FIG. 10, a line 113 indicates the difference in units of degrees between the phase $\phi(k)$ vs. frequency data of FIG. 8 and the fit determined from parameters of Eq. 7. The extent of nonlinearity $\epsilon\phi_2$ of line 113 as determined by the peak-to-valley range of the difference between phases $\phi(k)$ and the fit to the phases is about 5°.

We now discuss various methods for positioning one or more compensating optical elements along an optical path of an interferometer to compensate for optical thickness mismatch.

Figure 11:
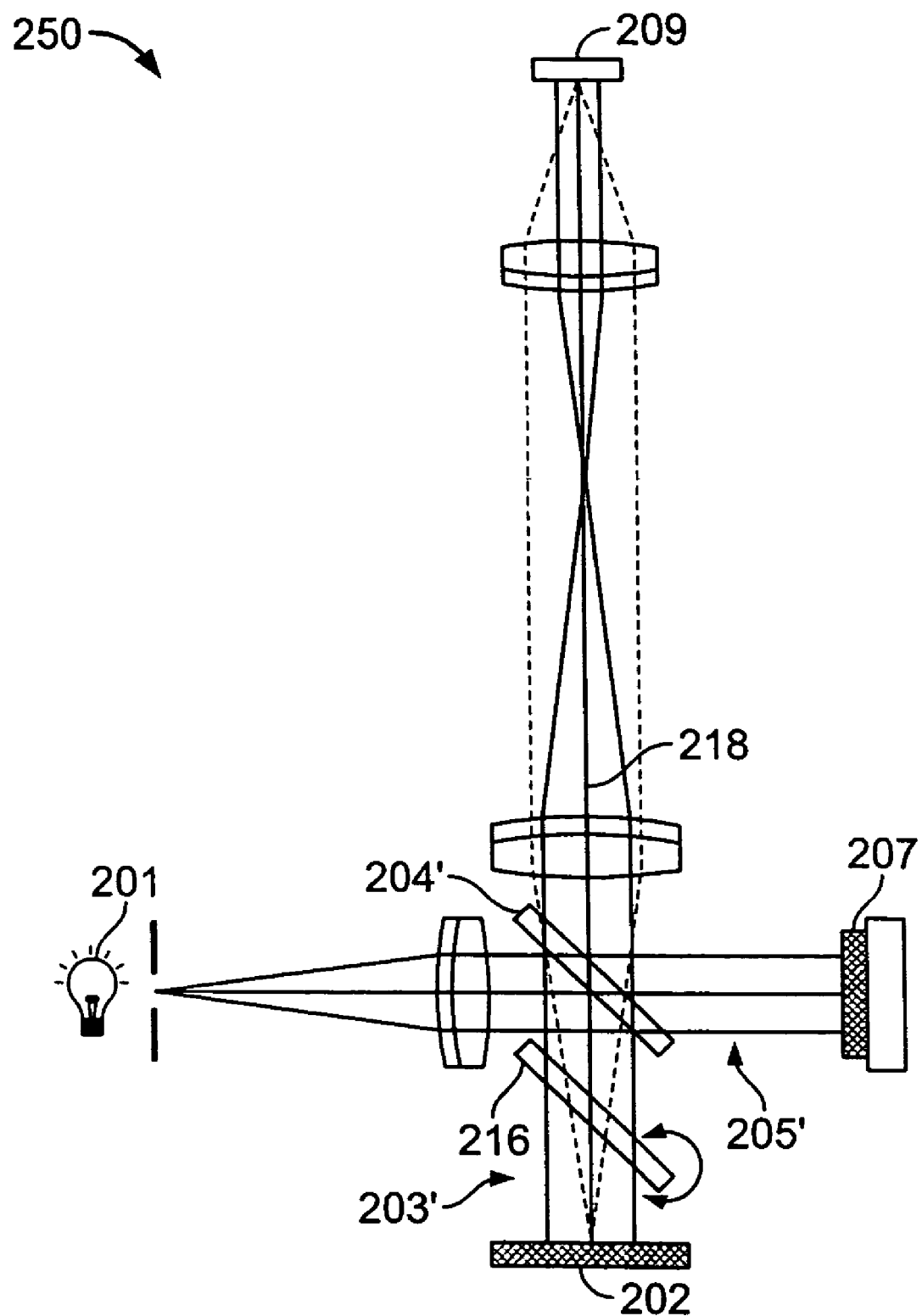
FIG. 11 illustrates an interferometer having a compensating optical element that can reduce dispersion mismatch.

Referring to FIG. 11, an example of compensating for optical thickness mismatch is shown for an interferometer 250 having a beam splitter formed as a plate 204', a test arm 203', and a reference arm 205'. A compensating optical element (e.g., a plate 216) is positioned along test arm 203'. Plate 216 can be rotated about an axis perpendicular to an optical axis 218 of interferometer 250 to introduce a variable compensation for optical thickness mismatch.

Figure 12:
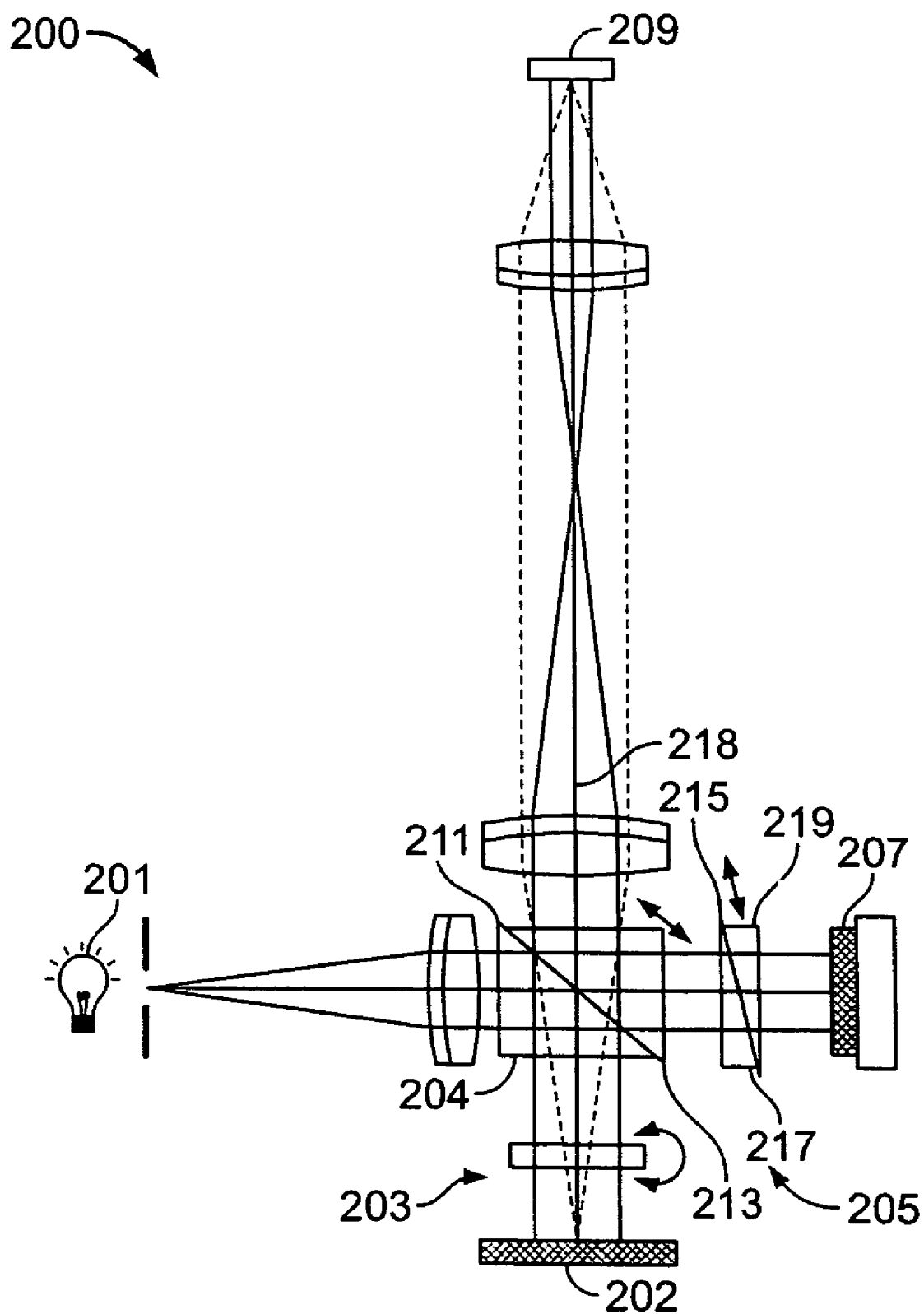
FIG. 12 illustrates an interferometer having a compensating optical element that can reduce dispersion mismatch.

Referring to FIG. 12, a Michelson interferometer is an example of an interferometer that can be used to obtain information about a test object 202. Light from a light source 201 is collimated and distributed by a beam splitter 204 between a test arm 203 and reference arm 205 of the interferometer. The light reflects from the light reflects from the test object 202 and a reference object 207, light is recombined by beam splitter 204 and interferes at a detector 209.

One source of optical thickness mismatch is beam splitter 204 because light traveling along the test arm 203 typically traverses a different thickness of the beam splitter than light traveling along the reference arm 205. One method for correcting the optical thickness mismatch is to split the beam splitter into first and second halves 211, 213. Each half 211, 213 can be slid with respect to the other to modify the thickness of the beam splitter traversed by light traveling along the test and reference arms.

Interferometers having beam splitters are described in U.S. patent application Ser. No. 10/659,060 filed Sep. 9, 2003 by Peter de Groot, which application is incorporated herein by reference.

As an alternative or in combination to beam splitter 204, an adjustable optical element (e.g., a split plate 215) can be positioned along one of the test and reference arms. Plate 215 includes first and second wedges 217, 219 that can be translated with respect to one another to modify the thickness traversed by the light traveling along reference arm 205. Typically, a fixed plate of the same nominal thickness as the split plate is positioned other arm.

If more than one compensating optical medium is used, the methods described above can be combined. For example, a split beam splitter or plate formed of two halves of a different optical medium can be used.

In another example, an optical plate is positioned along each arm of an interferometer. Each plate has the same nominal thickness. A correction is introduced by a rotation of one plate about an axis perpendicular to the optical axis of the system.

Figure 13:
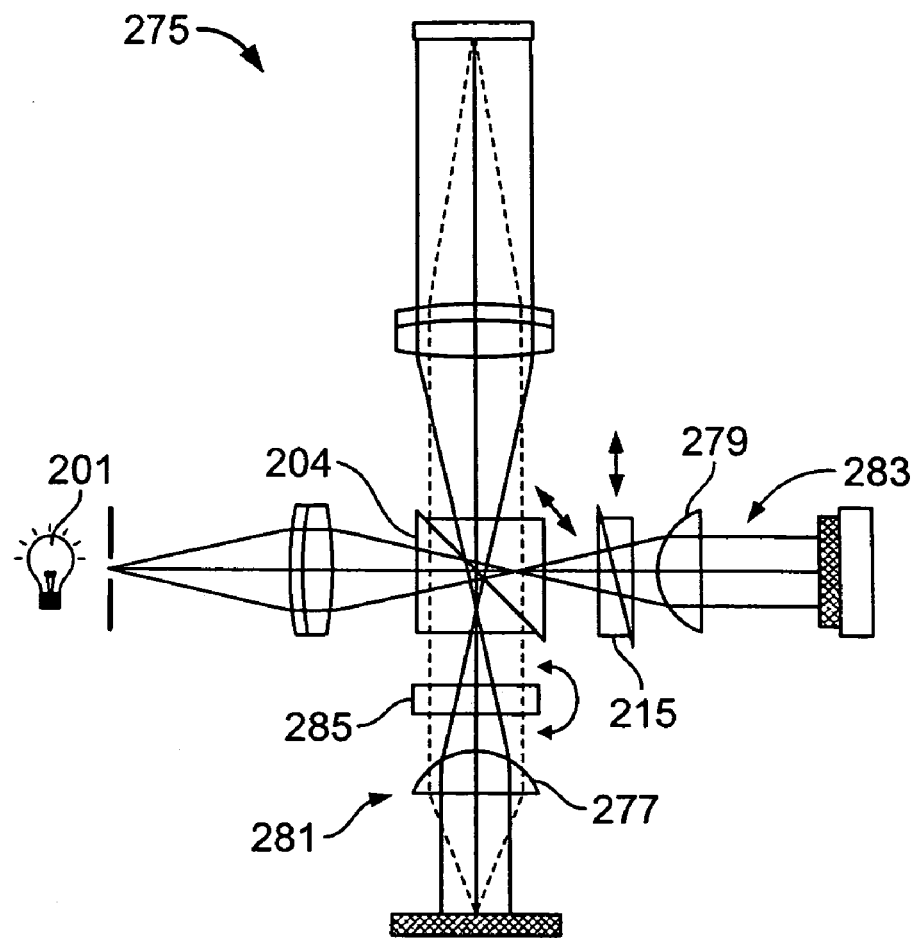
FIG. 13 illustrates an interferometer having a compensating optical element that can reduce dispersion mismatch.

Referring to FIG. 13, a Linnik interferometer 275 includes first and second objectives 277, 279 respectively positioned along test and reference arms 281, 283 of the interferometer. Each objective includes a plurality of optical elements (e.g., multiple lenses). Typically, compensating optical elements (e.g., beam splitter 204, split plate 215, and/or rotating plate 285) are positioned at locations in which light rays that originate from individual object points are parallel to one another.

While configurations for correcting optical thickness mismatch have been described as being uniform across a field of view of an interferometer, other configurations can be used. For example, in some embodiments, the optical thickness mismatch determined from interference signals that correspond to different spatial locations of the test object may be different (e.g., the optical thickness mismatch may vary across the field of view of the interferometer). The presence of a field dependent optical thickness mismatch can be determined based on multiple interference signals each corresponding to a different spatial location of the test object. As discussed next, a field dependent optical thickness mismatch can be compensated for by using one or more optical elements having a property (e.g., a shape, a thickness, and/or refractive index) that varies as a function of position in the field of view.

Figure 14:
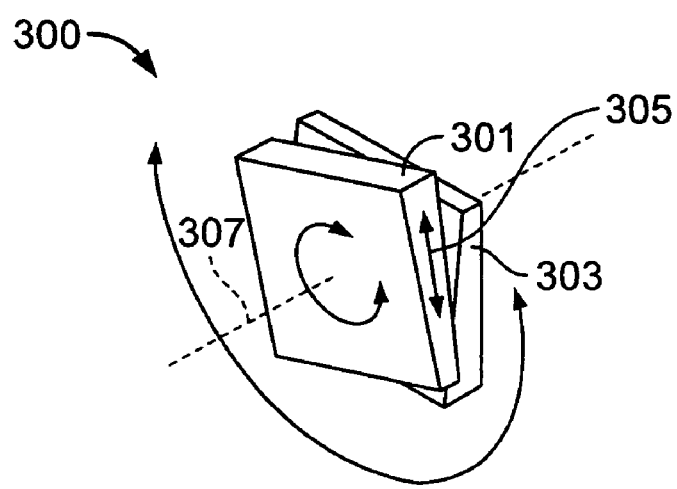
FIG. 14 illustrates a compensating optical element that can be used to reduce field dependent dispersion mismatch.

As seen in FIG. 14, a compensating optical element 300 includes first and second prisms 301, 303 that can be translated with respect to one another (e.g., along an axis 305) and rotated with respect to one another about an optical axis of an interferometer (e.g., about an axis 307). Additionally, optical element 300 can be rotated in its entirety about the optical axis of the interferometer.

The nominal thickness of optical element 300 can be changed by translating of one of prisms 301, 303 with respect to the other prism to adjust the average optical thickness mismatch compensation across the field the view. The field position dependent thickness of optical element 300 can be changed by rotating one of prisms 301, 303 about axis 307 with respect to the other prism to introduce a field dependent optical thickness mismatch compensation. Typically, an optical element for providing field dependent optical thickness mismatch compensation is positioned at an intermediate image of the object or is positioned close to the test object.

While methods for compensating for optical thickness mismatch have been described as including the use of a compensating optical element, other methods can be used. For example, in some embodiments, the information about an optical thickness mismatch is related to the position of an optical element (e.g., a decenter, a tip, a tilt, and/or a longitudinal spacing of the optical element). Typically, the optical element is a refractive optical element (e.g., a lens or lens system (e.g., an objective). Because refractive elements can introduce varying amounts of optical thickness as a function of the position of the refractive element with respect to the optical axis of the interferometer, it can be important to match this field-dependent parameter in the test and reference arms in order to obtain high-contrast interference signals. The performance of interferometers such as Linnik or Twyman-Green interferometers that include multiple refractive elements is particularly sensitive to the position of optical elements.

Typically, a method for determining information about an optical thickness mismatch related to a position of an optical element includes obtaining interference signals from each of multiple spatial locations of a test object using an interferometer. Phase $\phi(k)$ vs. frequency data are determined for each of the interference signals. The extent of non-linearity (e.g., $\epsilon\phi$) is determined for each phase $\phi(k)$ vs. frequency data and mapped according to position within the field of the interferometer. For a perfectly aligned interferometer, the map of extent of the non-linearity of the phase $\phi(k)$ vs. frequency data is rotationally symmetrical function about the optical axis of the interferometer. If a refractive component (e.g., an lens or lens system (e.g., an objective) is misaligned in one of the arms of the interferometer (e.g., decentered, tipped, and/or tilted), then the non-linearity phase map will no longer be symmetrical. For example, decenter of a component yields to first order a tilt of the non-linearity map. This overall effect can be understood from the fact that optical thickness mismatches can typically be modeled as a spherical function. Decenter of one objective results in a shear of this spherical function, resulting in a tilted plane. In those cases, the gradient of the non-linearity map can be used as a quantitative feedback signal for alignment. The optical element can be repositioned based on the information about the optical thickness mismatch and an iterative method used to determine the optimal position.

In some situations, the map of the phase nonlinearity as a function of field position includes more complicated radial patterns such that the effect of a decenter is no longer well approximated by a tilt. Nevertheless, the argument that the map should be a symmetric function when alignment is optimum still holds. Hence, more advanced processing of the map of the phase nonlinearity as a function of field position using, for example, Zernike polynomials, or simple visual observation, can still provide quantitative or qualitative information about misalignment of one or more optical elements.

As discussed above, lateral aberrations are another source of error that can be introduced by interferometers. We next discuss examples of lateral aberrations and methods for determining the presence of lateral aberrations and reducing the same.

Referring back to FIG. 1, detector 59 of interferometer system 50 includes multiple detector elements. In an ideal interferometer, the interferometer focuses light reflected from different spatial locations of the test object to sharp, distinct foci at different detector elements. In practice, the foci corresponding to different spatial locations of the test object can contain some amount of aberration (e.g., blur). Lateral aberration is one type of aberration that can blur the foci corresponding to spatial locations of a test object.

Figure 15:
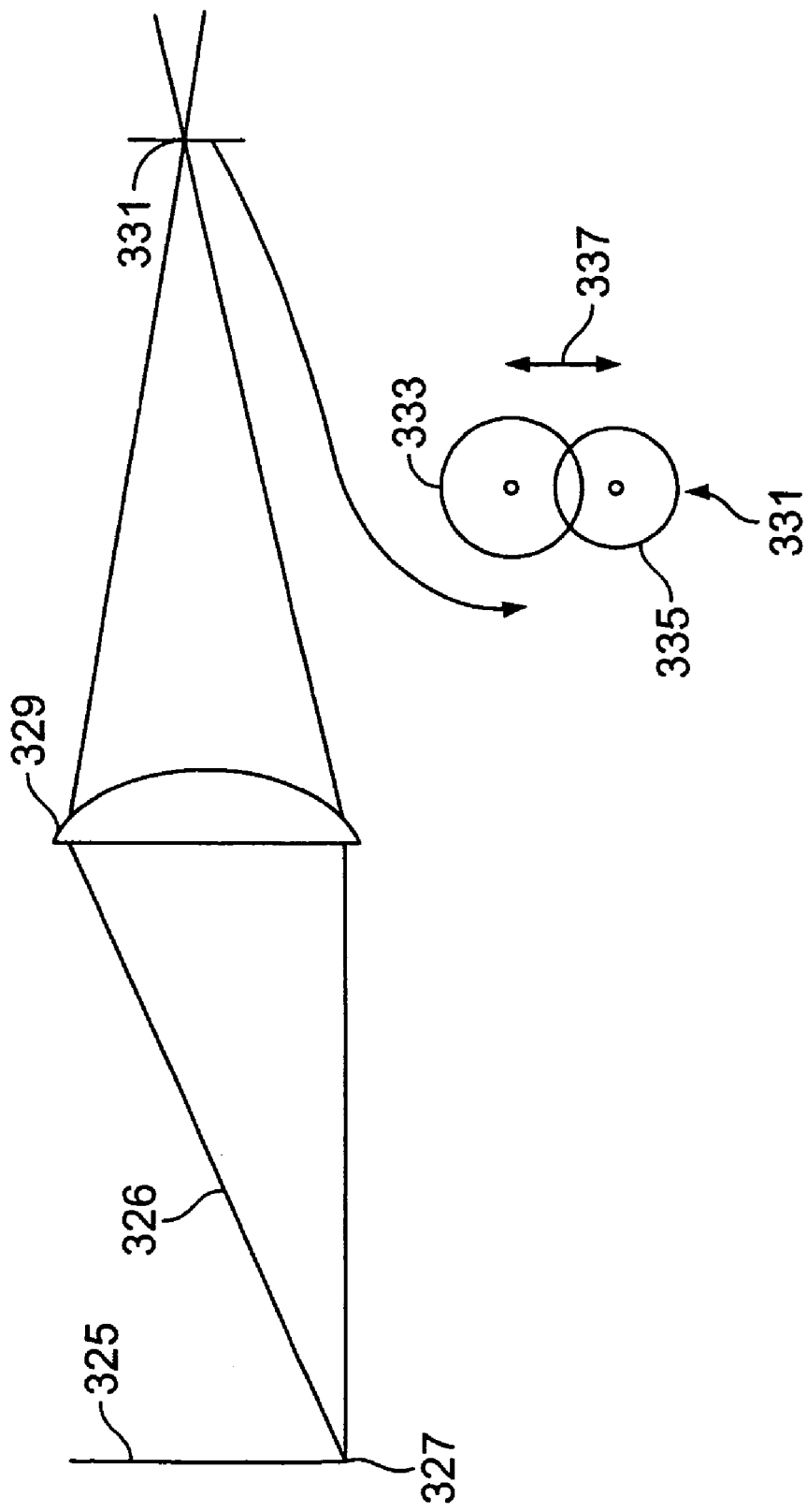
FIG. 15 illustrates a wavelength dependent lateral aberration.

FIG. 15 illustrates lateral color, a wavelength dependent lateral aberration. Lateral color results because refractive optics (e.g., lenses and lens systems) typically focus light of different wavelengths at different lateral locations with respect to the optical axis. For example, FIG. 15 shows a light beam 326 having first and second different wavelengths reflected from a spatial location 327 of a test object 325. A lens 329 focuses light beam 326 to a focus 331, which includes a spot 333 corresponding to light of the first wavelength and a spot 335 corresponding to light of the second wavelength of beam 326. Spots 333, 335 are spaced apart by a distance 337 that corresponds to a wavelength dependent lateral aberration of lens 329. In an interferometer, light reflected from each spatial location of a test object may be focused into a blurry focus including multiple spots each corresponding to different wavelength components of the illuminating light.

Figure 16:
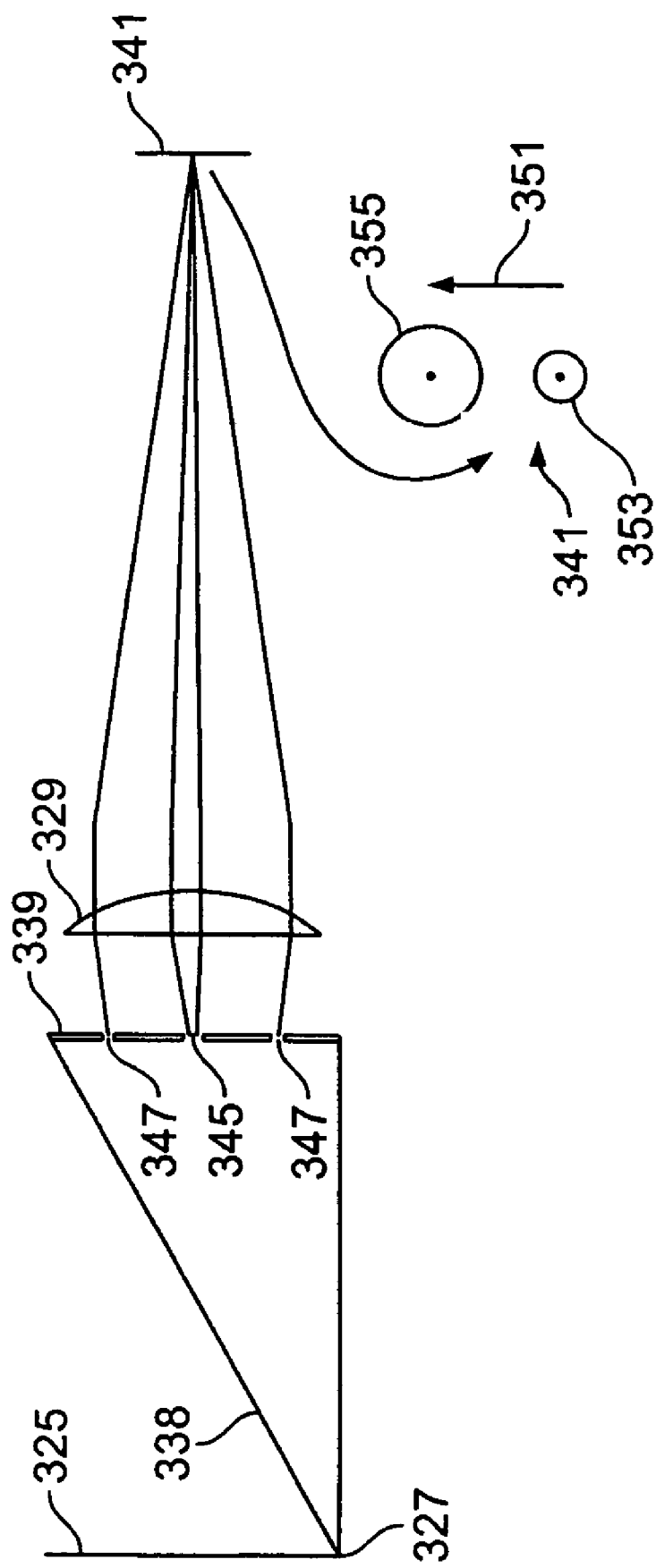
FIG. 16 illustrates a geometry dependent lateral aberration.

FIG. 16 illustrates coma, a geometry dependent lateral aberration. Coma results because optics (e.g., lenses and lens systems) focus light to a location and shape that depends on the geometry of the path traveled by the focused light. For example, FIG. 16 shows a monochromatic light beam 338 reflected from spatial location 327 of test object 325. For illustration purposes, a spatial filter having first and second annuli 345, 347 is positioned between object 325 and lens 329. Annulus 345 allows only light having small angles of incidence to pass through. Annulus 347 allows only light have a large angle of incidence to pass through. Lens 329 focuses light passing through first and second annuli 345, 347 to a focus 341 including a spot 343 corresponding to light passing through annulus 345 and a spot 355 corresponding to light passing through annulus 347. Spots 343, 345 are spaced apart by a distance 351 that corresponds to a geometry dependent lateral aberration of lens 329. In an interferometer, light reflected from each spatial location of a test object may be focused into a blurry focus including multiple spots each corresponding to different angles of incidence traversed by the illuminating and/or reflected light.

As discussed above, low coherence interference signals typically include interference at each of multiple frequencies k that correspond to the spectral distribution of the light source (e.g., the range of emission wavelengths) and the geometric properties of optical elements of the interferometer (e.g., the angles of incidence with which the light is received and transmitted by the optical elements of the interferometer). One limiting case is an interferometer that uses a low numerical aperture illumination and imaging system, and a relatively broad source spectrum. In such interferometers, the range of illumination wavelengths may be large and the range of angles of incidence is small. The frequencies k of interference signals obtained with these interferometers correspond to the spectral distribution of the light source. Consequently, the lateral aberrations in such interferometers tend to be dominated by wavelength dependent lateral aberrations (e.g., as shown in FIG. 15).

Another limiting case is a high-numerical aperture interferometer where the light source is spatially extended but is nominally monochromatic. In such interferometers, the range of wavelengths is small and the range of angles of incidence is large. The frequencies k of interference signals obtained with these interferometers correspond to the spatial frequencies resulting from geometric properties of optical elements of the interferometer. Consequently, the lateral aberrations in such interferometers tend to be dominated by geometry dependent lateral aberrations (e.g., as shown in FIG. 16).

We next discuss methods for determining information related to lateral aberration of one or more optical elements (e.g., a lens or lens system). The optical element(s) can be, for example, an optical element of an interferometer or an optical element to be tested (e.g., during manufacture). Typically, the methods include using the optical element to determine information related to multiple spatial locations of a patterned test object (e.g., determining an image, phase profile, and/or height profile of the test object) for each of first and second illumination conditions (e.g., different illumination wavelengths or different illumination geometries (e.g., different angles of incidence)). Information related to lateral aberrations is determined from the information related to the multiple spatial locations determined under the different illumination conditions. In general, the determination includes a cross-correlation of information determined under the first illumination condition and information determined under the second illumination condition.

Figure 17:
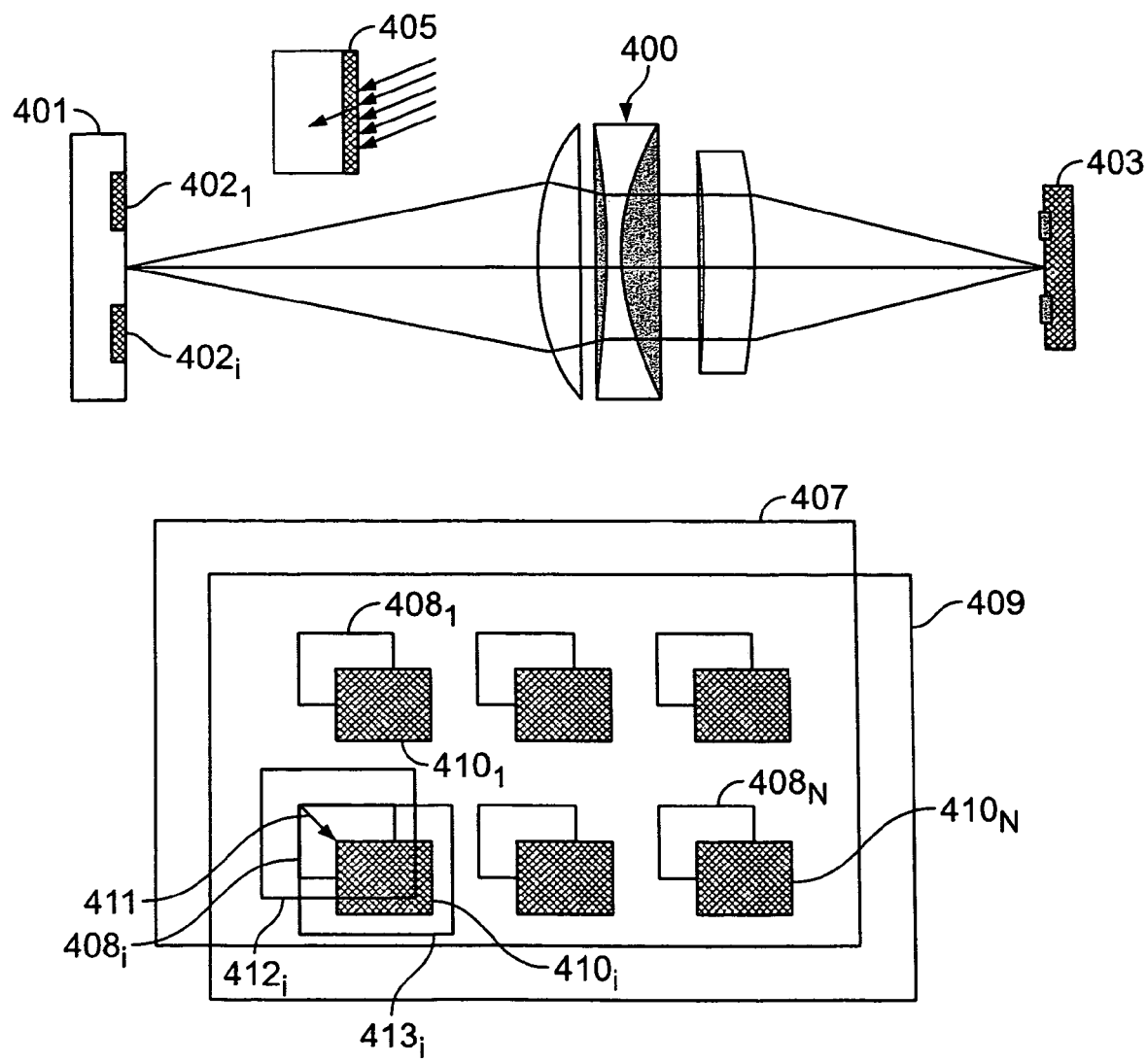
FIG. 17 illustrates determining information related to a wavelength dependent lateral aberration of an optical element.

With reference to FIG. 17, some embodiments of the method include determining information related to wavelength dependent lateral aberrations of an optical element (e.g., a lens system 400). Typically, the optical element is configured to image a patterned test object 400 onto a detector 403 having multiple detector elements (e.g., a CCD having multiple pixels). Test object 401 includes multiple surface features 402i (e.g., multiple step features). A spectral filter 405 is used to illuminate the object with generally monochromatic light having a first central wavelength. Typically, the test object is illuminated with a narrow range of angles of incidence. An image 407 of the test object is obtained with the light having the first central wavelength. Spectral filter 405 is then configured to illuminate the test object with generally monochromatic light having a different central wavelength. An image 409 of the test object is obtained with the light having the second central wavelength.

Image 407 includes image features 408i corresponding to surface features 402i of patterned test object 401. Image 409 includes image features 410i corresponding to surface features 402i of patterned test object 401. Because of wavelength dependent lateral aberrations, image features 408i and image features 410i are shifted with respect to one another. For example, a vector 411 indicates the magnitude and direction of the image feature shift between image feature 408i of image 407 (corresponding to surface feature 402i) and image feature 410i of image 409 (also corresponding to surface feature 402i). Vector 411 is indicative of a wavelength dependent lateral aberration of optical element 400 at a position within its field of view corresponding to surface feature 402i.

The wavelength dependent lateral aberration at a field position corresponding to surface feature 402i (e.g., vector 411) can be determined by cross-correlating a sub-region 412i of image 407 with a sub-region 413i of image 409. Sub-regions 412i and 413i are nominally centered on the same surface feature (e.g., surface feature 402i)) and have the same width and height in terms of detector pixels. The cross-correlation typically includes transforming each image sub-region into an inverse domain. The transformation is generally a two-dimensional transformation and can be accomplished by, for example, Fourier transformation. Vector 411 is determined based on the transformed sub-regions.

In some embodiments, the cross-correlation includes determining a phase map corresponding to each transformed sub-region. Phase unwrapping is used to prepare an unwrapped phase map that is a linear function of spatial frequency. The phase gradient in the vertical and horizontal directions yields the magnitude and direction of the shift (e.g., vector 411) of the surface feature between the transformed sub-regions.

In some embodiments, the cross-correlation includes determining the product of the Fourier transform of one sub-region and the conjugate of the Fourier transform of the other sub-region. The product is inverse transformed (e.g., by inverse Fourier transformation). The magnitude and direction of the shift of the surface features (e.g., vector 411) can be determined from a peak in the inverse transformed product.

In general, the image sub-regions are scaled prior to transformation to make them as similar as possible in amplitude. An image sub-region can be scaled by, for example, subtracting the average of the sub-region from each pixel of that sub-region and then dividing each pixel by the standard deviation of the average subtracted pixels.

The wavelength dependent lateral aberration of optical element 400 can be determined for each of multiple field positions by determining the magnitude and direction of the shift corresponding to image sub-regions distributed across the field of view of the optical element. As discussed below, the lateral aberrations so determined can be expressed as a vector map indicative of the field-dependent lateral aberration.

Figure 18:
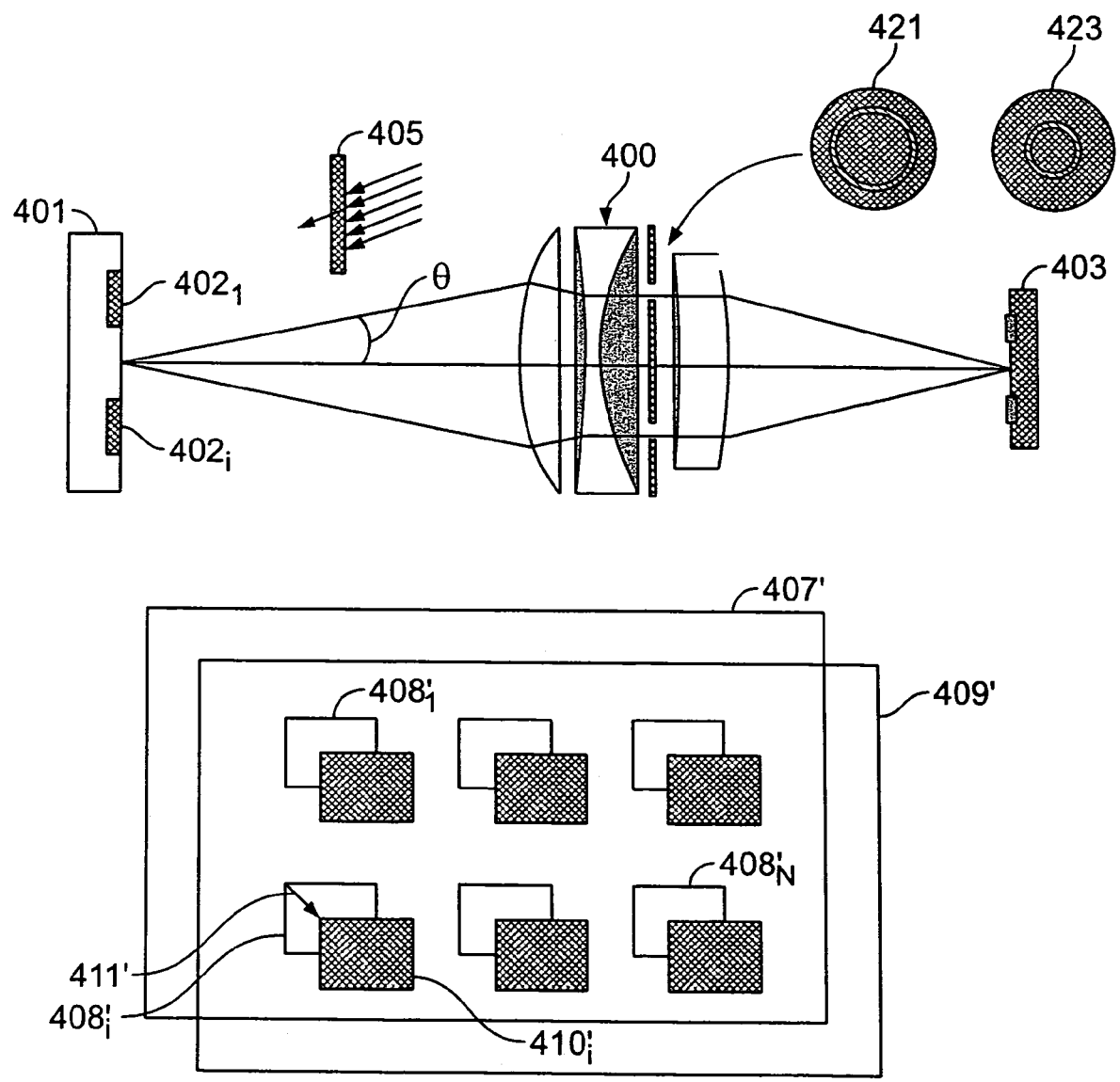
FIG. 18 illustrates determining information related to a geometry dependent lateral aberration of an optical element.

With reference to FIG. 18, some embodiments of the method include determining information related to geometry dependent lateral aberrations of an optical element (e.g., of lens system 400). The optical element is configured to image patterned test object 400 onto detector 403. Typically, the test object is illuminated by generally monochromatic light having a wide range of angles of incidence. An image 407' of the test object is obtained using a first annulus 421 that accepts only light having a narrow range of angles of incidence centered about a first angle θ. An image 409' of the test object is obtained using a second annulus 423 that accepts only light having a narrow range of angles of incidence centered about a second angle different from angle θ.

Image 407' includes image features 408'i corresponding to surface features 402i of patterned test object 401. Image 409' includes image features 410'i corresponding to surface features 402i of patterned test object 401. Because of geometry dependent lateral aberrations, image features 408'i and image features 410'i are shifted with respect to one another. For example, a vector 411' indicates the magnitude and direction of the image feature shift between image feature 408'i of image 407' (corresponding to surface feature 402i) and image feature 410'i of image 409' (also corresponding to surface feature 402i). Vector 411' is indicative of a geometry dependent lateral aberration of optical element 400 at a position within its field of view corresponding to surface feature 402i.

Vector 411' can be determined using correlation techniques as described above. Information related to geometry dependent lateral aberrations of optical element 400 can be determined for multiple positions within the field of view of the optical element (e.g., a vector map of the geometry dependent lateral aberration can be prepared).

Figure 19:
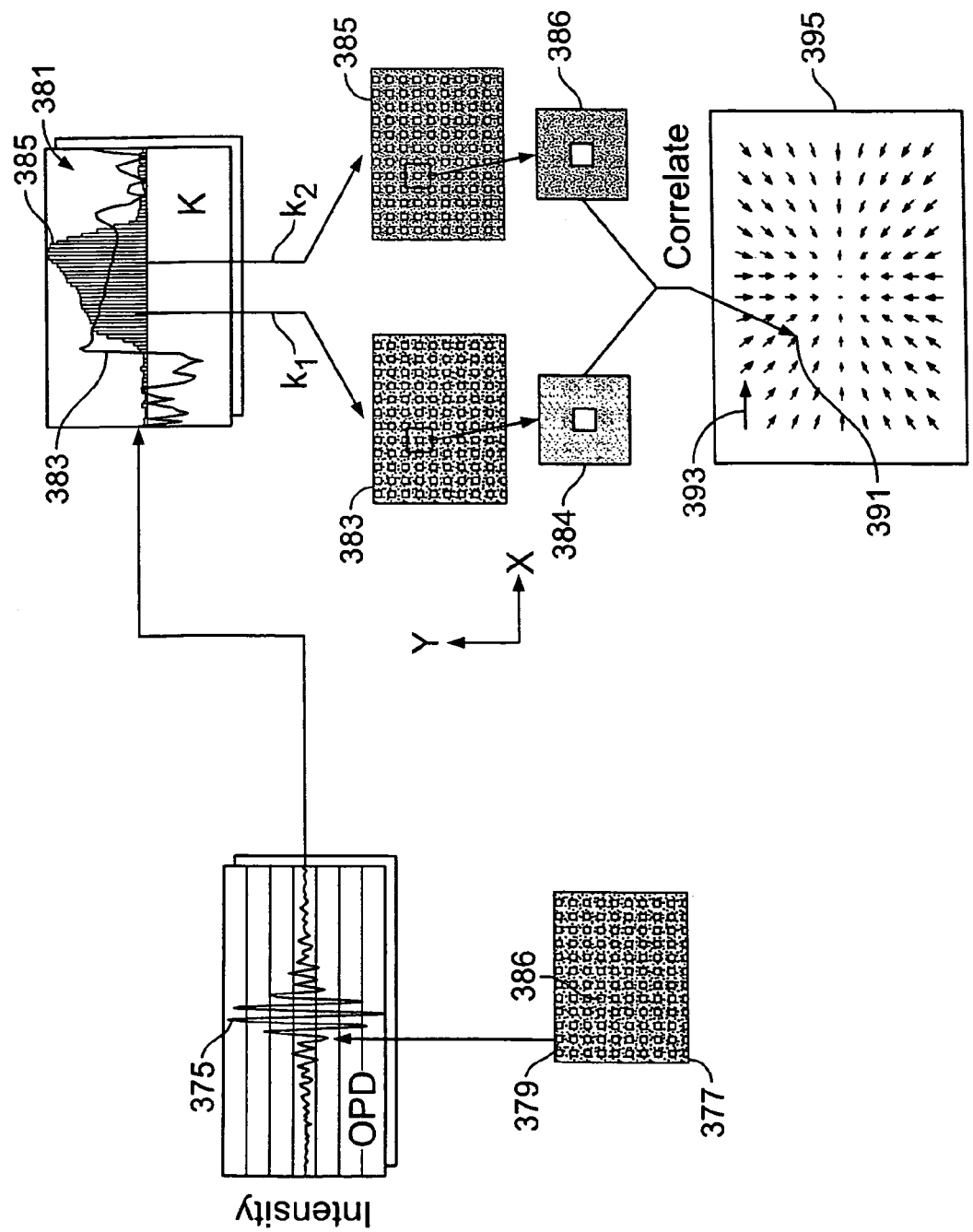
FIG. 19 illustrates determining information related to a lateral aberration of an interferometer.

With reference to FIG. 19, some embodiments of the method include using an interferometer to determine information related to a lateral aberration of an optical element (e.g., an optical element(s) of the interferometer or a test optical element(s)). The method typically includes obtaining an interference signal from each of multiple spatial locations of a patterned test object 377. Typically, the interferometer is configured so that either wavelength dependent lateral aberration (e.g., a generally low numerical aperture and generally broad source spectrum) or geometry dependent lateral aberration (e.g., a generally high numerical aperture and generally narrow source spectrum) will dominate. By way of example, FIG. 19 shows an interference signal 375 corresponding to a single spatial location 379 of the test object 377 obtained under conditions in which wavelength dependent lateral aberration will dominate.

Each interference signal is transformed into an inverse dimension (e.g., by Fourier transformation) with respect to OPD to prepare a transformed interference signal. By way of example, FIG. 19 shows a transformed interference signal 381 corresponding to the transform of interference signal 375.

Figure 20A:
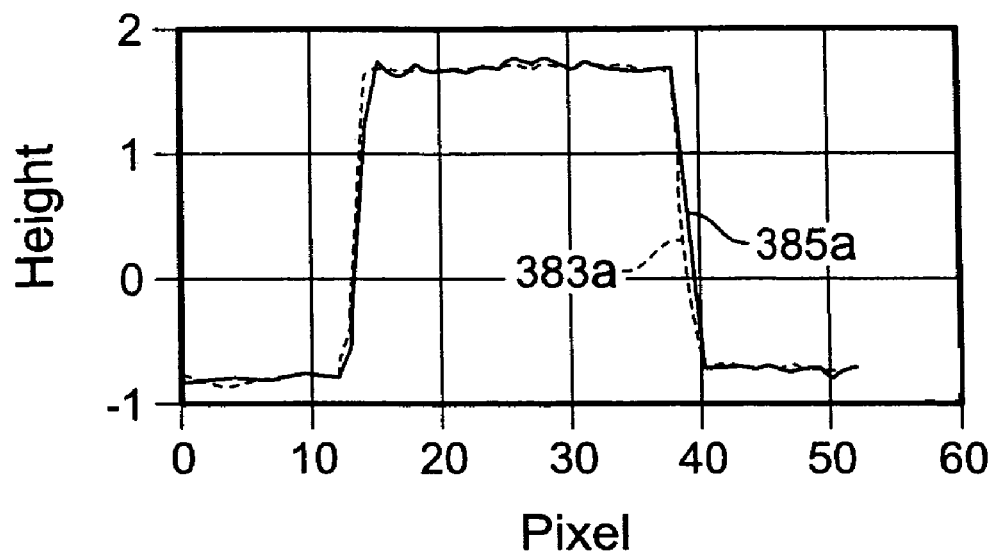
FIGS. 20A and 20B illustrate cross sections through phase profiles shown in FIG. 19.
Figure 20B:
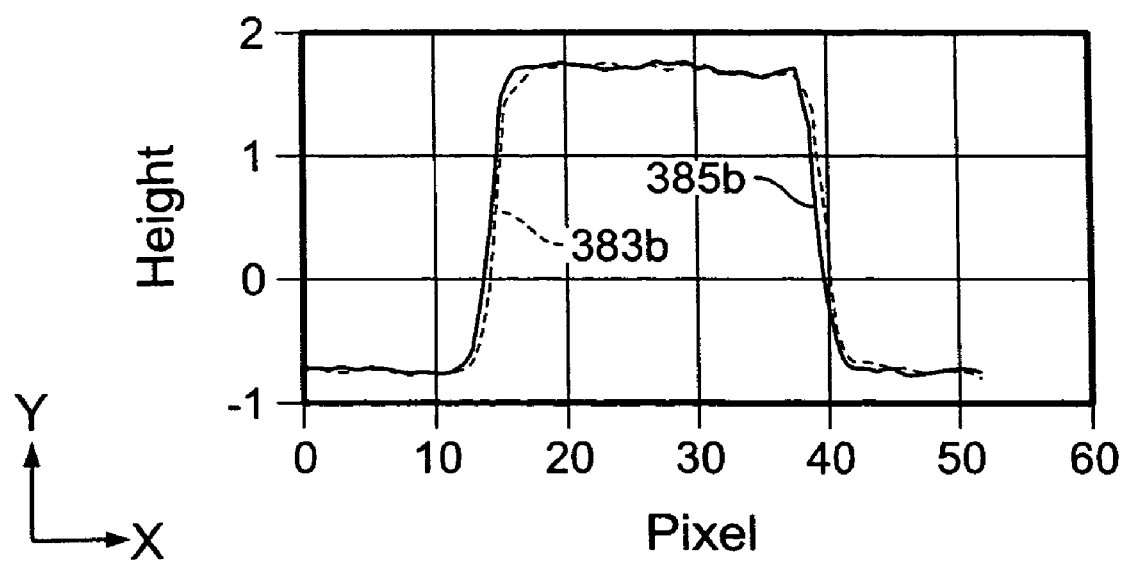

Transformed interference signal 381 includes a phase component 383 and an amplitude component 385. The phase component 383 is indicative of the phase φ(k) of each frequency k of the interference signal. The amplitude component 385 is indicative of the amplitude of each frequency k of the interference signal. For each transformed interference signal, the phase φ(k) and/or amplitude components at each of two different frequencies k are used to determine information related to multiple spatial locations of patterned test object 377 (e.g., a phase profile, and/or height profile of the test object). For example, a phase profile 383 is prepared based on the phase φ(k) and/or amplitude at a frequency k1 corresponding to a source wavelength of 516 nanometers and a phase profile 385 is prepared based on the phase φ(k) and/or amplitude at a frequency k2 corresponding to a source wavelength 618 of nanometers. FIG. 20A illustrates a cross section 383a through sub region 383 (dashed line) and a cross section 385a through sub region 385 (solid line) each along the y-dimension. FIG. 20B illustrates a cross section 383b through sub region 383 (dashed line) and a cross section 385b through sub region 385 (solid line) each along the x-dimension.

Pairs of corresponding sub-regions of each phase profile are selected (e.g., based on a regular arrangement of sub-regions across the phase profiles). Each pair of corresponding sub-regions includes information related to the same surface feature and is centered about the same nominal location of the test object. For example, a sub-region 384 includes phase profile information related to a surface feature 386 of 377 as determined from frequency k1 and a sub-region 386 includes phase profile information related to a surface feature 386 of 377 as determined from frequency k2. Corresponding sub-regions of phase profiles 383 and 385 are cross-correlated to determine information related to the lateral aberrations of the interferometer. For example, a vector 391 corresponding to the wavelength dependent lateral aberration at a field position corresponding to surface feature 386 is determined by cross-correlating sub-regions 384, 386. The length of an arrow 393 corresponds to a vector magnitude of one detector pixel. Vectors determined from multiple pairs of corresponding sub-regions can be presented as a vector map indicative of the field dependent wavelength dependent lateral aberration of the interferometer.

While the forgoing method has been described as using an interferometer configured so that either wavelength or geometry dependent lateral aberration will dominate, other methods can be used. For example, wavelength dependent lateral aberration can be determined at high numerical aperture by making multiple measurements at each of different wavelengths (e.g., by narrowly filtering a broadband source under high numerical aperture illumination conditions). Alternatively, wavelength dependent lateral aberration can be determined in an interferometer nominally configured for high numerical aperture illumination (e.g., by spatially filtering a broadband source to reduce geometrical lateral aberration as compared to wavelength dependent lateral aberration).

We next discuss exemplary applications of methods for determining information related to lateral aberration (e.g., a vector map of wavelength dependent and/or geometry dependent lateral aberration).

In some embodiments, information related to lateral aberration is used to position one or more optical components of an interferometer. For example, information related to lateral aberration can be used as a manufacturing feedback mechanism to assist determining the center, tilt, tip, and/or longitudinal spacing of an optical element that reduces lateral aberration. The positioning is typically based on information related to lateral aberrations over the entire field of view of the interferometer.

Typically, the method includes determining first information related to lateral aberration. For example, a first vector map can be prepared based on interference signals obtained with optical elements of the interferometer in a first position. The position (e.g., center, tilt, tip, and/or lateral spacing) of one or more of the optical elements (e.g., objective) is modified. A second vector map is prepared based on interference signals obtained with the optical elements of the interferometer in the modified position. The first and second vector maps can be compared to determine whether the lateral aberrations were reduced or increased by the modified position of the optical element(s). For example, the magnitude of vectors within the vector maps can be compared. This process can continue iteratively until, for example, lateral aberrations have been reduced to less than a determined level.

As an example, consider that the camera lens of a microscope objective can be positioned over a range of distances from the pupil of the microscope objective (e.g., the longitudinal spacing between the camera lens and pupil can vary (e.g., over tens of millimeters)). Such microscope objectives can be positioned along an optical path of an interferometer. Vector maps obtained at different longitudinal positions of the camera lens and pupil can be used to reduce lateral aberration that results from improper longitudinal spacing between the camera lens and pupil. Such vector maps can also be used to determine, for example, a center, a tip, and a tilt of the lens that reduces lateral aberration.

Figure 21:
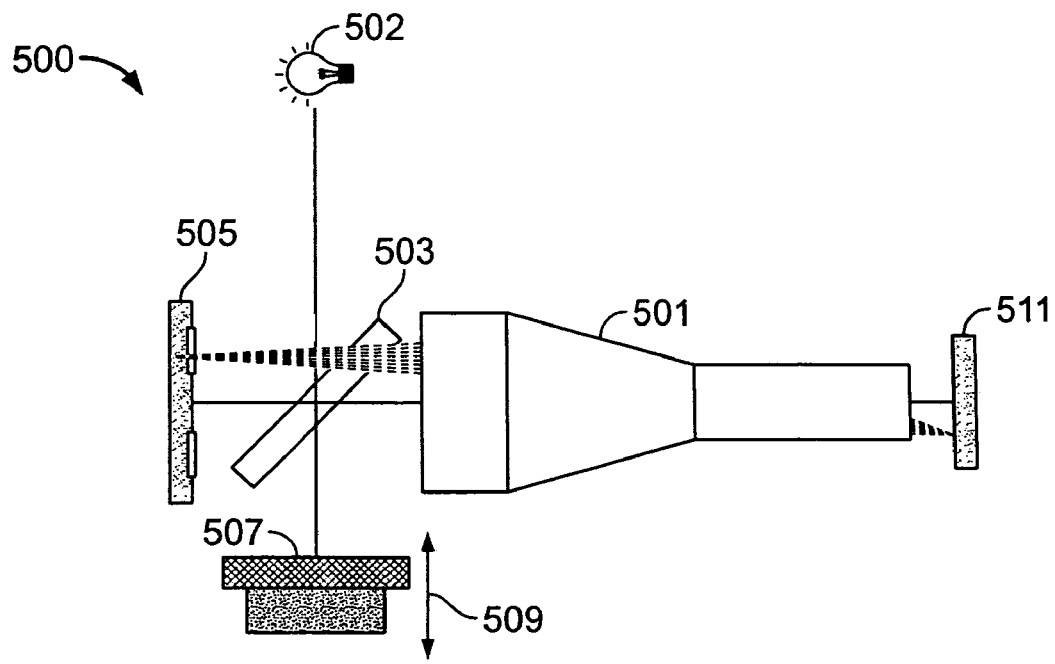
FIG. 21 illustrates a system for determining information related to a lateral aberration of an optical element.

Referring to FIG. 21, a 500 for determining a lateral aberration of an optical element (e.g., a telecentric lens system 501) includes a light source 502, a beam splitter 503, a patterned test object 505, a reference object 507 movable along a scan dimension 509, and a multidimensional detector 511. Light source 502 can be configured to illuminate object 505 with, for example, broadband light having a low numerical aperture (e.g., using a spatial filter to restrict angles of incidence) or narrow band light having a high numerical aperture (e.g., using a spectral filter to restrict wavelengths of the illuminating light). The lateral aberration of lens system 501 can be determined based on, for example, information related to multiple spatial locations of a patterned test object (e.g., an image, phase profile, and/or height profile of the test object) and cross-correlation of sub-regions of the information related to the spatial locations as discussed above. For example, a vector map of geometry and/or wavelength dependent lateral aberrations can be determined. Optical elements of lens system 501 can be iteratively adjusted based on the information about the lateral aberration. Lateral aberration of lens system 501 can be compared to lateral aberration of reference lens.

Figure 22:
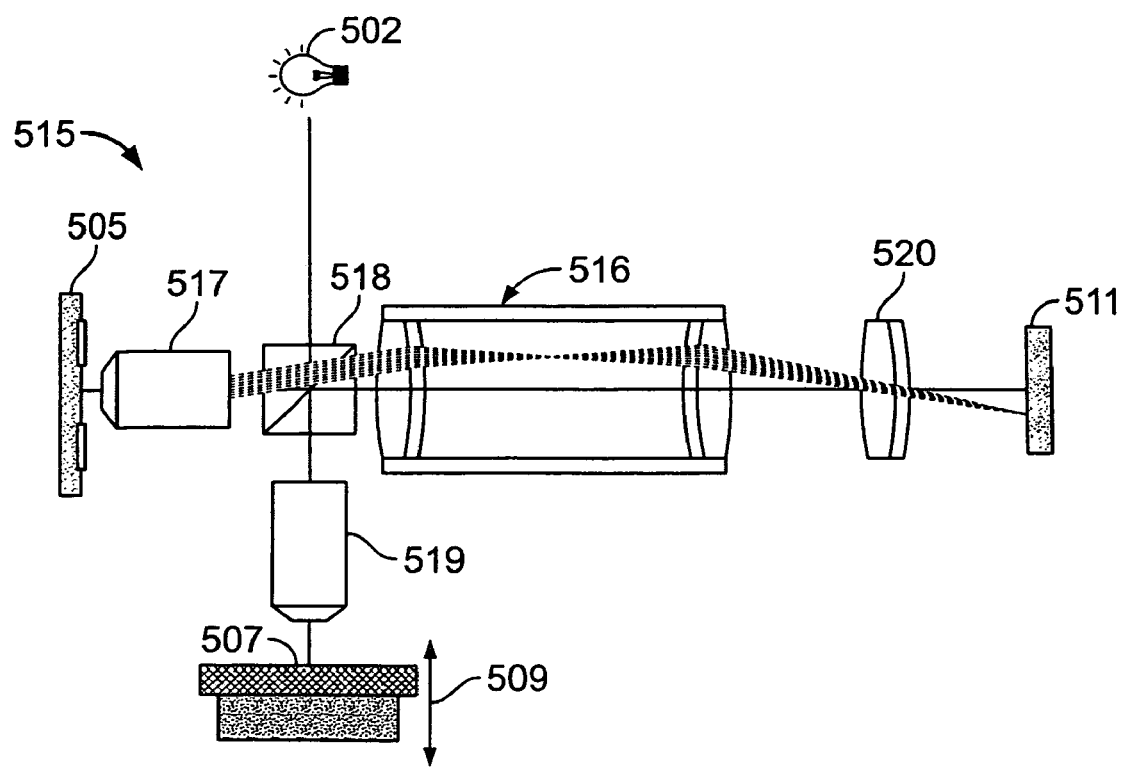
FIG. 22 illustrates a system for determining information related to a lateral aberration of an optical element.

Referring to FIG. 22, a system 515 for determining a lateral aberration of an optical element (e.g., afocal lens system 516) includes a light source 502, a beam splitter 518, patterned test object 505, reference object 507 movable along scan dimension 509, a pair of microscope objectives 517, 519, an optic 520 (e.g., an infinite conjugate objective), and multidimensional detector 511. System 515 can be used as system 500 (e.g., to iteratively adjust optical elements of lens system 516 and/or compare lateral aberration of lens system 501 to lateral aberration of a reference lens).

While systems 500 and 515 have been described as being used to determine a lateral aberration of a particular optical element, such systems can be used to determine a lateral aberration of other optical elements as well. In general, an interferometer can be used to determine a lateral aberration of any optical element positioned along an optical path of the interferometer. The lateral aberration that is determined may be the contribution of the optical element to the total lateral aberration of all the optical elements of the interferometer.

While a method for determining information about lateral aberration has been described as being based on light reflected from a patterned test object, other test objects may be used. For example, the test object may have random surface features (e.g., surface roughness due to machining and/or chemical etching). Correlation can be performed on sub-regions defined by, for example, a regular sampling array.

While a method for determining information about lateral aberration has been described as being based on information about a test object determined from each of two different frequencies, more frequencies of the interference signals can be used. For example, use of more than two frequencies can provide information about the lateral aberrations over a greater range of wavelengths of the light source and angles of incidence. Additionally, if more than two frequencies are used, the correlation can be performed using information about the test object determined from more closely spaced frequencies. By using multiple correlation steps across most (e.g., all) of the range of frequencies corresponding to the effective spatial frequency spectrum of the interferometer it is possible to provide information between frequencies that are so widely separated that direct correlation would be poor, for example because of the blurring of images at different colors.

As discussed above, information about the test object (e.g., a reflectivity image, a phase profile, or a height profile) can be determined based on interference signals from a test object. Also as discussed above, information about the test object (e.g., a reflectivity image, a phase profile, or a height profile) can be determined based on each of multiple frequency components of the interference signals. For example, as discussed with respect to FIG. 19, height profiles of an object can determined from each of different frequency components of interference signals.

The ITF of an interferometer is indicative of the response of the interferometer to height variations of a test object along the scan dimension. Typically, the height variations are expressed as a height profile of the test object. A height profile of a test object can be determined from, for example, phase information of interference signals obtained from the test object. For example, FIGS. 19, 20A and 20B illustrate height profiles of sharp surface features of a test object generated using phase information at each of two different frequency components of multiple interference signals.

The ITF of an interferometer can be determined based upon a test object height profile determined based on interference signals obtained with the interferometer. Typically, an ITF is determined by, for example, Fourier transforming a height profile and determining the ratio of the transformed height profile spectrum and a reference Fourier transform (e.g., the Fourier transform of a reference surface feature (e.g., a surface feature having a step function in height)). An ITF can be determined for each of multiple positions within a field of view of the interferometer (e.g., the ITF can be determined based on the height profiles of each of multiple sub-regions of a test object).

An ITF can be determined based upon each of multiple height profiles where each height profile is determined from a different frequency component of interference signals from a test object. Each ITF is indicative of the response of the interferometer to height variations of the test object at the wavelength of light that corresponds to the frequency component used to prepare the height profile for that ITF. Hence, the multiple ITF's can be used to determine information related the wavelength dependence of the ITF for the interferometer.

The MTF of an interferometer is indicative of the response of the interferometer to reflectivity variations along a lateral dimension of a test object test. Typically, the reflectivity variations are expressed as an image of the test object.

The MTF of an interferometer can be determined based upon an image of the test object. Typically, an MTF is determined by, for example, Fourier transforming an image of a test object and determining the ratio of the transformed image and a reference Fourier transform (e.g., the Fourier transform of a reference surface feature (e.g., a surface feature having sharp reflectivity transition)). An MTF can be determined for each of multiple positions within a field of view of the interferometer (e.g., the MTF can be determined based on the images of each of multiple sub-regions of a test object).

An MTF can be determined based upon each of multiple images where each image is determined from a different frequency component of interference signals from a test object. Each MTF is indicative of the response of the interferometer to reflectivity variations of the test object at the wavelength of light that corresponds to the frequency component used to prepare the height profile for that MTF. Hence, the multiple MTF's can be used to determine information related the wavelength dependence of the MTF for the interferometer.

The location and orientation of the discontinuous features of a test object used to determine the ITF and/or MTF can be chosen to measure these properties in various directions (vertically, horizontally, radially or tangentially for example), which allows studying the structure of certain types of non-symmetrical aberrations.

Note that in some cases additional information may be gained by moving the detector through focus and repeating the measurement.

While scanning interferometry data have been described as being obtained by varying an OPD (e.g., by moving a test and/or reference object), other configurations are possible. For example, in some embodiments, scanning interferometry data are obtained by varying a wavelength of that light interferes at the detector. Each scan position typically corresponds to a different wavelength of detected interfering light (e.g., to a different central wavelength of the detected interfering light). Each scan position increment typically corresponds to a difference in the wavelength between scan positions.

Any of the methods described above can be implemented, for example, in computer hardware, software, or a combination of both. The methods can be implemented in computer programs using standard programming techniques following the descriptions herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

Other aspects, features, and advantages are within the scope of the invention.

What is claimed is:

1. A method comprising:
   providing scanning interferometry data of a test object, wherein:
   the scanning interferometry data comprises an interference signal for each of multiple spatial locations of the test object,
   each interference signal comprises an interference intensity value for each of multiple scan positions of the interferometer;
   determining first information about the object based on a frequency component of each of the interference signals; and
   determining second information about the object based on a second frequency component of each of the interference signals, the second frequency component not used in the determination of the first information about the object.

2. The method of claim 1, wherein the scanning interferometry data were obtained by a method comprising passing light through an optical element, and the method further comprises determining information related to the optical element based on the first and second information about the test object.

3. The method of claim 2, wherein the information related to the optical element is related to a lateral aberration of the optical element.

4. The method of claim 3, wherein determining the first and second information comprises transforming each interference signal into a frequency domain with respect to scan values for the scan positions of the interferometer.

5. The method of claim 4, wherein the determination of the first information is based on at least one of a phase and a magnitude corresponding to the first frequency of each transformed interference signal and the determination of the second information is based on at least one of a phase and a magnitude corresponding to the second frequency of each transformed interference signal.

6. The method of claim 3, wherein the optical element is positioned along an optical axis of an arm of the interferometer.

7. The method of claim 6, wherein the optical element is a lens system including multiple lenses.

8. The method of claim 6, further comprising moving the optical element relative to an optical axis of the arm of the interferometer in response to the information related to the lateral aberration.

9. The method of claim 6, further comprising deciding to replace the optical element with a second optical element based on the information related to the lateral aberration.

10. The method of claim 3, wherein the optical element is positioned along an optical axis between an arm of the interferometer and a detector of the interferometer.

11. The method of claim 3, wherein the first frequency component of each interference signal results from interference of light having a first wavelength and the second frequency component of each interference signal results from interference of light have a second wavelength.

12. The method of claim 3, wherein the first frequency of each interference signal results from interference of light that illuminates the test object with a first angle of incidence and the second frequency of the interference signal results from interference of light that illuminates the test object with a second, different angle of incidence.

13. The method of claim 2, wherein:
the first information about the object is related to a first height profile of the test object;
the second information about the object is related to a second height profile of the test object; and
the method further comprises determining a first instrument transfer function of the interferometer based on the first height profile and determining a second instrument transfer function of the interferometer based on the second height profile.

14. The method of claim 2, wherein:
the first information about the object is related to a first reflectivity profile of the test object;
the second information about the object is related to a reflectivity height profile of the test object; and
the method further comprises determining a first modulation transfer function of the interferometer based on the first reflectivity profile and determining a second modulation transfer function of the interferometer based on the second reflectivity profile.

15. The method of claim 2, wherein:
the first information about the object is related to a first reflectivity profile of the test object;
the second information about the object is related to a reflectivity height profile of the test object; and
the method further comprises determining a first modulation transfer function of the optical element based on the first reflectivity profile and determining a second modulation transfer function of the optical element based on the second reflectivity profile.

16. The method of claim 1, wherein the determination of the first information about the object is further based on one or more additional frequency components and the determination of the second information about the object is further based on one or more additional frequency components.

17. The method of claim 1, further comprising outputting information based on the first and second determined information.

18. A method comprising:
providing first image data of an object, the first image data having been obtained by passing first light through an optical element, the first light having a first central wavelength;
providing second image data of the object, the second image data having been obtained by passing second light through the optical element, the second light having a second central wavelength different from the first central wavelength, the step of passing the second light through the optical element being performed after the step of passing the first light through the optical element;
cross-correlating at least a portion of the first image data and a corresponding portion of the second image data; and
determining information about the optical element based on the cross-correlation of the first and second image data.

19. The method of claim 18, wherein the information related to the optical element is related to a lateral aberration of the optical element.

20. The method of claim 18, further comprising outputting information based on the determined information about the optical element based on the cross-correlation.

* * * * *